(12) United States Patent
Singh et al.

(10) Patent No.: US 11,435,347 B2
(45) Date of Patent: *Sep. 6, 2022

(54) METHODS FOR PREDICTION OF ANTI-TNF α DRUG LEVELS AND AUTOANTIBODY FORMATION

(71) Applicant: PROMETHEUS LABORATORIES INC., San Diego, CA (US)

(72) Inventors: Sharat Singh, San Diego, CA (US); Venkateswarlu Kondragunta, San Diego, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 16/687,373

(22) Filed: Nov. 18, 2019

(65) Prior Publication Data

US 2020/0158725 A1 May 21, 2020

Related U.S. Application Data

(63) Continuation of application No. 15/486,072, filed on Apr. 12, 2017, now Pat. No. 10,571,467, which is a continuation of application No. PCT/IB2015/058048, filed on Oct. 19, 2015.

(60) Provisional application No. 62/086,103, filed on Dec. 1, 2014, provisional application No. 62/065,997, filed on Oct. 20, 2014.

(51) Int. Cl.
| | | |
|---|---|---|
| *G01N 33/564* | (2006.01) | |
| *G01N 33/50* | (2006.01) | |
| *G01N 33/68* | (2006.01) | |
| *G01N 33/94* | (2006.01) | |

(52) U.S. Cl.
CPC ....... *G01N 33/564* (2013.01); *G01N 33/5091* (2013.01); *G01N 33/6869* (2013.01); *G01N 33/94* (2013.01); *G01N 2333/5421* (2013.01); *G01N 2333/5434* (2013.01); *G01N 2800/065* (2013.01); *G01N 2800/52* (2013.01)

(58) Field of Classification Search
CPC ............. G01N 33/564; G01N 33/5091; G01N 33/6869; G01N 33/94; G01N 2333/5421; G01N 2800/065; G01N 2800/52

See application file for complete search history.

(56) References Cited

U.S. PATENT DOCUMENTS

| | | | |
|---|---|---|---|
| 5,750,355 A | 5/1998 | Targan et al. | |
| 5,830,675 A | 11/1998 | Targan et al. | |
| 6,218,129 B1 | 4/2001 | Walsh et al. | |
| 8,450,069 B2 | 5/2013 | Goix et al. | |
| 8,574,855 B2 | 11/2013 | Singh et al. | |
| 9,079,949 B1 * | 7/2015 | Andrien, Jr. | ............... A61P 3/10 |
| 10,571,467 B2 | 2/2020 | Singh et al. | |
| 2007/0172483 A1 | 7/2007 | Schwaeble et al. | |
| 2008/0026485 A1 | 1/2008 | Hueber et al. | |
| 2012/0329172 A1 | 12/2012 | Singh et al. | |
| 2014/0051184 A1 | 2/2014 | Singh et al. | |

FOREIGN PATENT DOCUMENTS

| | | |
|---|---|---|
| WO | WO-2008036802 A2 | 3/2008 |
| WO | WO-2008036802 A3 | 5/2008 |
| WO | WO-2009012140 A2 | 1/2009 |
| WO | WO-2009012140 A3 | 3/2009 |
| WO | WO-2009108637 A1 | 9/2009 |
| WO | WO-2010132723 A1 | 11/2010 |
| WO | WO-2011008990 A1 | 1/2011 |
| WO | WO-2011050069 A1 | 4/2011 |
| WO | WO-2011056590 A1 | 5/2011 |
| WO | WO-2012088337 A1 | 6/2012 |
| WO | WO-2012119113 A2 | 9/2012 |
| WO | WO-2012154987 A1 | 11/2012 |
| WO | WO-2013033623 A1 | 3/2013 |
| WO | WO-2016063204 A1 | 4/2016 |

OTHER PUBLICATIONS

Toichi et al. (J. Immunol. 2006 177:4917-4926) (Year: 2006).*
Steenholdt Scandinavian J. Gastroenterology 2011 46: 310-318 (Year: 2011).*
Afif et al.: Clinical utility of measuring infliximab and human anti-chimeric antibody concentrations in patients with inflammatory bowel disease. American Journal of Gastroenterology 105(5):1133-1139 (2010).
Bendtzen et al.: Individualized monitoring of drug bioavailability and immunogenicity in rheumatoid arthritis patients treated with the tumor necrosis factor α inhibitor infliximab. Arthritis & Rheumatism 54(12): 3782-3789 (2006).
Breiman: Random Forests. Machine Learning, 45; 5-32 (2001) http://stat-www.berkeley.edu/users/breiman/RandomForests/cc_home.htm.
Freeman et al.: Neural Networks: Algorithms, Applications and Programming Techniques. Addison-Wesley Publishing Company; 414 pages (1991).
International Application No. PCT/IB2015/058048 International Search Report and Written Opinion dated Apr. 28, 2016.
Jones et al.: Structure of tumour necrosis factor. Nature, 338:225-228 (1989).

(Continued)

*Primary Examiner* — Changhwa J Cheu
(74) *Attorney, Agent, or Firm* — Wilson Sonsini Goodrich & Rosati

(57) ABSTRACT

In some aspects, the present invention provides methods for predicting whether a subject will develop autoantibodies to an anti-TNFα drug during the course of anti-TNFα drug therapy. In other aspects, the present invention provides methods for predicting the level of an anti-TNFα drug in a subject during the course of anti-TNFα drug therapy. Systems for predicting anti-TNFα drug levels and the likelihood of autoantibody formation during the course of anti-TNFα drug therapy are also provided herein. The present invention further provides methods for predicting a clinical outcome (e.g., endoscopic response) of a subject on anti-TNFα drug therapy.

16 Claims, 37 Drawing Sheets

(56) References Cited

OTHER PUBLICATIONS

Klimiuk et al.: Regulation of serum chemokines following infliximab therapy in patients with rheumatoid arthritis; Clinical Experimental Rheumatology; vol. 24, 529-533 (2006).

Pennica et al.: Human tumour necrosis factor: precursor structure, expression and homology to lymphotoxin. Nature, 312; 724-729 (1984).

Pittoni et al.: Anti-tumour necrosis factor (TNF) α treatment of rheumatoid arthritis (infliximab) selectively down regulates the production of interleukin (IL)18 but not of IL12 and IL13; Ann Rheum Dis; vol. 61, 723-725 (2002).

R&D Systems: Recombinant Human TNF-α. Catalog No. 210-TA, Minneapolis, MN (2018).

Steinberg et al.: CART: Tree Structured Non-Parametric Data Analysis. Salford Systems. 355 pages (1995).

Zadeh: Fuzzy Sets. Information and Control; 8:338-353 (1965).

Zadeh: Outline of a New Approach to the Analysis of Complex Systems and Decision Processes. IEEE Trans. on Systems. Man and Cybernetics; 3:28-44 (1973).

Holers et al., The alternative pathway of complement in disease: opportunities for therapeutic targeting. Mol Immunol. 41(2-3):147-152 (2004).

Holers, The spectrum of complement alternative pathway-mediated diseases. Immunol Rev. 223:300-316 (2008).

* cited by examiner

| Time Point | TNF | IFX | CRP | HSA |
|---|---|---|---|---|
| Baseline | 0.1882 | | 0.5771 | 0.7114 |
| Week 2 | 0.839 | 0.0617 | 0.5669 | 0.5 |
| Week 6 | 0.4883 | <0.0001 | 0.4627 | 0.6359 |
| Week 14 | 0.0193 | <0.0001 | 0.0625 | 0.4781 |

*FIG. 2*

| Var 1 | Var 2 | Mono therapy (p-value) | Combination Therapy (p-value |
|---|---|---|---|
| IFX t2 (wk 2) | ATI week 6 | 0.19 | 0.78 |
| IFX t3 (wk 6) | ATI week 14 | 0.0006 | 0.1855 |
| IFX t4 (wk 14) | ATI week 14 | 0.0052 | 0.0013 |
| IFX t2 (wk 2) | ATI week 14 | 0.0556 | 0.69 |

FIG. 3

| IFX_T3_Quartiles | Total ATI Reported [U/ml]_t4 | |
|---|---|---|
| | Detectable | Not Detectable |
| 1(<11.79) | 21 | 30 |
| 2[11.79,20.2) | 21 | 27 |
| 3[20.2,34.38) | 6 | 44 |
| 4(>=34.28) | 4 | 45 |

| | IMM use during IFX induction | | | | | | | |
|---|---|---|---|---|---|---|---|---|
| | 0 | | | | 1 | | | |
| | Total ATI Reported [U/ml]_t4 | | | | Total ATI Reported [U/ml]_t4 | | | |
| | Not Detectable | | Detectable | | Not Detectable | | Detectable | |
| IFX_T3_Quartiles | CRP | CRP | CRP | CRP | CRP | CRP | CRP | CRP |
| 1(<11.79) | 11.35 | 12(57) | 4.7 | 9 | 8.3 | 5(25) | 4.7 | 15 |
| 2[11.79,20.2) | 1.3 | 8(47) | 2.1 | 9 | 3.9 | 9(34.6) | 1.9 | 17 |
| 3[20.2,34.38) | 1.85 | 2(18) | 1.5 | 9 | 1.1 | 3(8.57) | 1.5 | 32 |
| 4(>=34.28) | | 0 | 1.7 | 18 | 18.1 | 3(12.5) | 1.2 | 21 |

*FIG. 5*

| IFX_T4_Quartiles | Total ATI Reported [U/ml]_t4 | |
|---|---|---|
| | Detectable | Not Detectable |
| 1(<3.19) | 29 | 21 |
| 2[3.19,6.95) | 20 | 31 |
| 3[6.95,13.83) | 3 | 47 |
| 4(>=13.83) | 1 | 49 |

| IFX_T4_Quartiles | IMM use during IFX induction | | | | | | | |
|---|---|---|---|---|---|---|---|---|
| | 0 | | | | 1 | | | |
| | Total ATI Reported [U/ml]_t4 | | | | Total ATI Reported [U/ml]_t4 | | | |
| | Detectable | | Not Detectable | | Detectable | | Not Detectable | |
| | CRP | CRP | CRP | CRP | CRP | CRP | CRP | CRP |
| 1(<3.19) | 4.9 | 13(59) | 6.9 | 9 | 12.2 | 11(55) | 5 | 9 |
| 2[3.19,6.95) | 1.2 | 8(57) | 1.85 | 6 | 1 | 6(24) | 2.8 | 19 |
| 3[6.95,13.83) | 5 | 1(6.7) | 1.35 | 14 | 6.1 | 2(6) | 1.25 | 31 |
| 4(>=13.83) | | 0 | 1.7 | 16 | 24.5 | 1(3.5) | 1.35 | 28 |

FIG. 6

| Initial Predictor Variables in the model (Baseline) |
|---|
| TNF_T1 |
| CRP_w0 (mg/L) |
| Albumin_w0 (g/dL) |
| IMM |
| Gender |
| Age |
| Age at diagnosis |
| BMI at 1st IFX |
| hemoglobin at 1st IFX |
| Age at 1st IFX (years) |
| Surgery previous |

| Summary of Fit | |
|---|---|
| RSquare | 0.177541 |
| RSquare Adj | 0.155312 |
| Root Mean Square Error | 0.78653 |
| Mean of Response | 2.075828 |
| Observations (or Sum Wgts) | 153 |

Analysis of Variance

| Source | DF | Sum of Squares | Mean Square | F Ratio |
|---|---|---|---|---|
| Model | 4 | 19.76408 | 4.94102 | 7.9870 |
| Error | 148 | 91.55722 | 0.61863 | Prob > F |
| C. Total | 152 | 111.32130 | | <.0001* |

| Parameter Estimates | Estimate | Std Error | t Ratio | Prob>|t| |
|---|---|---|---|---|
| Intercept | 0.2502248 | 0.845313 | 0.30 | 0.7676 |
| Log[TNF_T1] | -0.165734 | 0.096386 | -1.72 | 0.0876 |
| Albumin_w0 (g/dL) | 0.3839698 | 0.179616 | 2.14 | 0.0342* |
| age | -0.013868 | 0.00496 | -2.80 | 0.0059* |
| BMI at 1st IFX | 0.038121 | 0.016401 | 2.32 | 0.0215* |

FIG. 7

Multiple regression model [IFX Reported [μg/mL] at week 2 after backward elimination

| Initial Predictor Variables in the model |
|---|
| TNF T1 |
| CRP_w0 (mg/L) |
| Albumin_w0 (g/dL) |
| IMM |
| Gender |
| Age |
| Age at diagnosis |
| BMI at 1st IFX |
| hemoglobin at 1st IFX |
| Age at 1st IFX (years) |
| Surgery previous |

Summary of Fit

| | |
|---|---|
| RSquare | 0.288273 |
| RSquare Adj | 0.271721 |
| Root Mean Square Error | 0.37523 |
| Mean of Response | 3.249359 |
| Observations (or Sum Wgts) | 177 |

Analysis of Variance

| Source | DF | Sum of Squares | Mean Square | F Ratio |
|---|---|---|---|---|
| Model | 4 | 9.808749 | 2.45219 | 17.4164 |
| Error | 172 | 24.217212 | 0.14080 | Prob > F |
| C. Total | 176 | 34.025961 | | <.0001* |

Parameter Estimates

| Term | Estimate | Std Error | t Ratio | Prob>|t| |
|---|---|---|---|---|
| Intercept | 1.3286544 | 0.367754 | 3.61 | 0.0004* |
| Log[CRP_w0 (mg/L)] | -0.040746 | 0.023475 | -1.74 | 0.0844 |
| Albumin_w0 (g/dL) | 0.3364555 | 0.079208 | 4.25 | <.0001* |
| Sex (Male=1, Female=0)[1] | -0.097552 | 0.028632 | -3.41 | 0.0008* |
| BMI at 1st IFX | 0.0268324 | 0.007213 | 3.72 | 0.0003* |

FIG. 8

| Initial Predictor variables considered in the Model |
| --- |
| TNF_T1 |
| CRP_w0 (mg/L) |
| Albumin_w0 (g/dL) |
| IMM use during IFX induction(0) |
| Gender |
| Age |
| Age at diagnosis |
| BMI at 1st IFX |
| Hemoglobin at 1st IFX |
| Age at 1st IFX (years) |
| Surgery previous |
| IFX Reported [µg/mL]_t2 |
| Total ATI Reported [U/mL]_T2 |
| TNF_t2 |
| CRP_w2 |
| Albumin_w2 |

| Summary of Fit | |
| --- | --- |
| RSquare | 0.411153 |
| RSquare Adj | 0.397924 |
| Root Mean Square Error | 0.592727 |
| Mean of Response | 2.936975 |
| Observations (or Sum Wgts) | 178 |

Analysis of Variance

| Source | DF | Sum of Squares | Mean Square | F Ratio |
| --- | --- | --- | --- | --- |
| Model | 4 | 42.50438 | 10.6261 | 30.2457 |
| Error | 173 | 60.77931 | 0.3513 | Prob > F |
| C. Total | 177 | 103.28368 | | <.0001* |

Parameter Estimates

| Term | Estimate | Std Error | t Ratio | Prob>|t| |
| --- | --- | --- | --- | --- |
| Intercept | -0.200911 | 0.351395 | -0.57 | 0.5682 |
| IMM use during IFX induction | -0.126567 | 0.046125 | -2.74 | 0.0067* |
| Surgery previous | 0.1056343 | 0.045918 | 2.30 | 0.0226* |
| Log[IFX Reported [µg/mL]_t2] | 0.9779335 | 0.104046 | 9.40 | <.0001* |
| Log[CRP_w2] | -0.086557 | 0.039135 | -2.21 | 0.0283* |

FIG. 9

Initial predictor variables Considered for the model

- TNF_T1
- CRP_w0 (mg/L)
- Albumin_w0 (g/dL)
- IMM use during IFX induction[0]
- Gender
- age
- Age at diagnosis
- BMI at 1st IFX
- Hemoglobin at 1st IFX
- Age at 1st IFX (years)
- Surgery previous
- IFX Reported [µg/mL]_t2
- Total ATI Reported [U/mL]_T2
- TNF_t2
- CRP_w2
- Albumin_w2
- IFX Reported [µg/mL]_T3
- Total ATI Reported [U/mL]_T3
- TNF_T3
- CRP_w6
- Albumin_w6

Summary of Fit

| | |
|---|---|
| RSquare | 0.529221 |
| RSquare Adj | 0.511522 |
| Root Mean Square Error | 0.585296 |
| Mean of Response | 1.981401 |
| Observations (or Sum Wgts) | 139 |

Analysis of Variance

| Source | DF | Sum of Squares | Mean Square | F Ratio |
|---|---|---|---|---|
| Model | 5 | 51.218005 | 10.2436 | 29.9020 |
| Error | 133 | 45.562070 | 0.3426 | Prob > F |
| C. Total | 138 | 96.780076 | | <.0001* |

Parameter Estimates

| Term | Estimate | Std Error | t Ratio | Prob>|t| |
|---|---|---|---|---|
| Intercept | -0.984426 | 0.417722 | -2.36 | 0.0199* |
| Age at 1st IFX | -0.009674 | 0.003538 | -2.73 | 0.0071* |
| Log[IFX Reported [µg/mL]_t2] | 0.704091 | 0.159121 | 4.42 | <.0001* |
| Log[IFX Reported [µg/mL]_T3] | 0.4769022 | 0.106667 | 4.47 | <.0001* |
| Total ATI Reported [U/mL]_T3 | 0.3926464 | 0.149196 | 2.63 | 0.0095* |
| Log[CRP_w6] | -0.077994 | 0.043435 | -1.80 | 0.0748 |

*FIG. 10*

| Variables Considered for the model |
|---|
| TNF_T1 |
| CRP_w0 (mg/L) |
| Albumin_w0 (g/dL) |
| IMM use during IFX induction |
| Gender |
| Age |
| Age at diagnosis |
| BMI at 1st IFX |
| Hemoglobin at 1st IFX |
| Age at 1st IFX (years) |
| Surgery previous to 1st IFX[1=yes, 0=no][0] |
| IFX Reported [µg/mL t2] |
| Total ATI Reported [U/ml T2] |
| TNF_t2 |
| CRP_w2 |
| Albumin_w2 |
| Log[IFX Reported [µg/mL] T3] |
| Total ATI Reported [U/ml T3][Detectable] |
| TNF_T3 |
| CRP_w6 |
| Albumin_w6 |

| Summary of Fit | |
|---|---|
| RSquare | 0.533644 |
| RSquare Adj | 0.512446 |
| Root Mean Square Error | 0.584743 |
| Mean of Response | 1.981401 |
| Observations (or Sum Wgts) | 139 |

| Analysis of variance | | | | | |
|---|---|---|---|---|---|
| Source | DF | Sum of Squares | Mean Square | F Ratio | |
| Model | 6 | 51.646074 | 8.60768 | 25.1742 | |
| Error | 132 | 45.134002 | 0.34192 | Prob > F | |
| C. Total | 138 | 96.780076 | | <.0001* | |

| Parameter Estimates | | | | |
|---|---|---|---|---|
| Term | Estimate | Std Error | t Ratio | Prob>|t| |
| Intercept | -1.139822 | 0.439829 | -2.59 | 0.0106* |
| Age at 1st IFX (years) | -0.01033 | 0.003584 | -2.88 | 0.0046* |
| Log[IFX Reported [µg/mL] t2] | 0.6839767 | 0.159984 | 4.28 | <.0001* |
| Log[IFX Reported [µg/mL] T3] | 0.5191526 | 0.113059 | 4.59 | <.0001* |
| Total ATI Reported [U/ml] T3 | 0.4139315 | 0.150264 | 2.75 | 0.0067* |
| Log[TNF_T3] | 0.0808579 | 0.072265 | 1.12 | 0.2652 |
| Log[CRP_w6] | -0.078694 | 0.043399 | -1.81 | 0.0721 |

*FIG. 11*

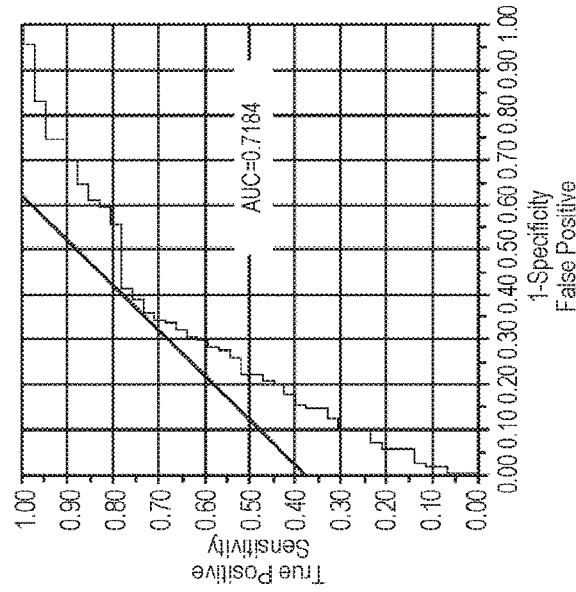

FIG. 12

| Initial Predictor Variables in the model |
|---|
| TNF_T1 |
| CRP_w0 (mg/L) |
| Albumin_w0 (g/dL) |
| IMM |
| Gender |
| Age |
| Age at diagnosis |
| BMI at 1st IFX |
| hemoglobin at 1st IFX |
| Age at 1st IFX (years) |
| Surgery previous |

| Summary of Fit | |
|---|---|
| RSquare (U) | 0.0973 |
| AICc | 183.976 |
| BIC | 199.414 |
| Observations (or Sum Wgts) | 174 |

| Analysis of variance | | | | |
|---|---|---|---|---|
| Model | -LogLikelihood | DF | ChiSquare | Prob>ChiSq |
| Difference | 9.354197 | 4 | 18.70839 | 0.0009* |
| Full | 86.809448 | | | |
| Reduced | 96.163644 | | | |

| Term | Estimate | Std Error | ChiSquare | Prob>ChiSq |
|---|---|---|---|---|
| Intercept | -6.655421 | 2.0494787 | 10.55 | 0.0012* |
| Log[TNF_T1] | 0.44767899 | 0.2641096 | 2.87 | 0.0901 |
| Sex (Male=1, Female=0)[1] | -0.6213053 | 0.2135074 | 8.47 | 0.0036* |
| Hb at 1st IFX | 0.40123357 | 0.1522939 | 6.94 | 0.0084* |
| IMM use during IFX induction[0] | 0.39050819 | 0.1898656 | 4.23 | 0.0397* |

Analysis of variance

| Model | -LogLikelihood | DF | ChiSquare | Prob>ChiSq |
|---|---|---|---|---|
| Difference | 12.333401 | 6 | 24.6668 | 0.0004* |
| Full | 75.677500 | | | |
| Reduced | 88.010902 | | | |

Summary of Fit

| | |
|---|---|
| RSquare (U) | 0.1401 |
| AICc | 166.107 |
| BIC | 186.749 |
| Observations (or Sum Wgts) | 157 |

| Term | Estimate | Std Error | ChiSquare | Prob>ChiSq |
|---|---|---|---|---|
| Intercept | -7.4766249 | 3.2802749 | 5.20 | 0.0227* |
| Log[TNF_T1] | 0.48831467 | 0.2826504 | 2.98 | 0.0841 |
| Albumin_w2 | 1.06859165 | 0.7044866 | 2.30 | 0.1293 |
| IMM use during IFX induction[0] | 0.37135061 | 0.2074669 | 3.20 | 0.0735 |
| Sex (Male=1, Female=0)[1] | -0.793499 | 0.2450968 | 10.48 | 0.0012* |
| Hb at 1st IFX | 0.50296842 | 0.1721888 | 8.53 | 0.0035* |
| Log[IFX Reported [µg/mL] t2] | -1.5600514 | 0.5369589 | 8.44 | 0.0037* |

Initial Predictor Variables in the model

- TNF_T1
- CRP_w0 (mg/L)
- Albumin_w0 (g/dL)
- IMM
- Gender
- Age
- Age at diagnosis
- BMI at 1st IFX
- hemoglobin at 1st IFX
- Age at 1st IFX (years)
- Surgery previous
- TNF 2
- CRP 2
- IFX 2

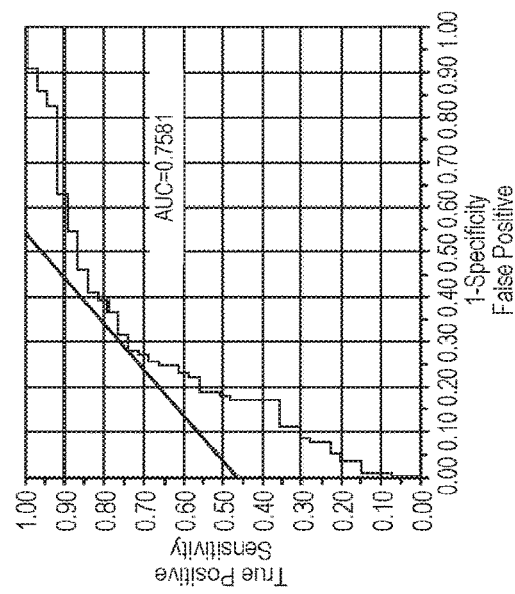

AUC=0.7581

FIG. 13

| Initial Variables in the model used up-to week 6 |
|---|
| Log[TNF_T1] |
| Log[CRP_w0 (mg/L)] |
| Albumin_w0 (g/dL) |
| IMM use during IFX induction[0] |
| Sex (Male=1, Female=0)[1] |
| age |
| Age at diagnosis of CD/IC/UC (years) |
| BMI at 1st IFX |
| Hb at 1st IFX |
| Age at 1st IFX (years) |
| Surgery previous to 1st IFX(1=yes, 0=no)[0] |
| Log[IFX Reported [µg/mL]_t2] |
| Total ATI Reported [U/ml_T2[Detectable] |
| Log[TNF_t2] |
| Albumin_w2 |
| Log[IFX Reported [µg/mL]_T3] |
| Total ATI Reported [U/ml_T3[Detectable] |
| Log[TNF_T3] |
| Log[CRP_w6] |
| Albumin_w6 |

| Model | -LogLikelihood | DF | ChiSquare | Prob>ChiSq |
|---|---|---|---|---|
| Difference | 18.827228 | 5 | 37.65446 | <.0001* |
| Full | 71.403351 | | | |
| Reduced | 90.230579 | | | |

Parameter Estimates

| Term | Estimate | Std Error | ChiSquare | Prob>ChiSq |
|---|---|---|---|---|
| Intercept | -9.3803366 | 3.4880015 | | |
| Albumin_w6 | 1.62043373 | 0.6982328 | 7.23 | 0.0072* |
| Hb at 1st IFX | 0.41616787 | 0.17077577 | 5.39 | 0.0203* |
| Log[IFX Reported [µg/mL]_T3] | -1.6167853 | 0.3792202 | 5.94 | 0.0148* |
| | | | 18.18 | <.0001* |
| Sex (Male=1, Female=0)[1] | -0.9339781 | 0.2670116 | 12.24 | 0.0005* |
| Log[TNF_T1] | 0.41035679 | 0.3106608 | 1.74 | 0.1865 |

| RSquare (U) | 0.2087 |
|---|---|
| AICc | 155.338 |
| BIC | 173.442 |
| Observations (or Sum Wgts) | 165 |

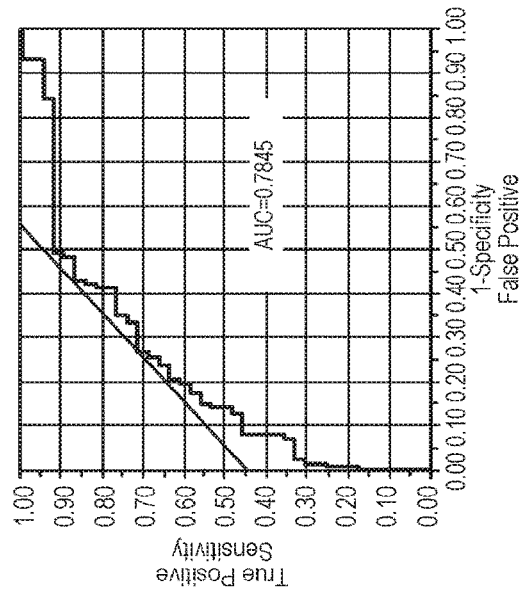

*FIG. 14*

| Initial Variables |
|---|
| TNF_T1 |
| CRP_w0 (mg/L) |
| Albumin_w0 (g/dL) |
| IMM use during IFX induction |
| Gender |
| Age |
| Age at diagnosis |
| BMI at 1st IFX |
| Hb at 1st IFX |
| Age at 1st IFX |
| Surgery previous |
| IFX Reported [µg/mL] |
| Total ATI Reported [U/mL]_T2[Detectable] |
| TNF_t2 |
| CRP_w2 |
| Albumin_w2 |
| IFX Reported [µg/mL]_t3 |
| Total ATI Reported [U/mL]_T3 |
| TNF_T3 |
| CRP_w6 |
| Albumin_w6 |
| TNF_t4 |
| IFX Reported [µg/mL]_t4 |
| CRP_w14 |
| Albumin_w14 |

| Model | -LogLikelihood | DF | ChiSquare | Prob>ChiSq |
|---|---|---|---|---|
| Difference | 40.882965 | 8 | 81.76593 | <.0001* |
| Full | 30.481090 | | | |
| Reduced | 71.364055 | | | |

| Term | Estimate | Std Error | ChiSquare | Prob>ChiSq |
|---|---|---|---|---|
| Intercept | -33.347126 | 8.7131301 | 14.65 | 0.0001* |
| Log[CRP_w0 (mg/L)] | 0.89553924 | 0.3036001 | 8.70 | 0.0032* |
| Sex (Male=1, Female=0)[1] | -1.6822029 | 0.4978014 | 11.42 | 0.0007* |
| Hb at 1st IFX | 0.73103016 | 0.2938817 | 6.19 | 0.0129* |
| Log[TNF_t2] | -3.8759689 | 1.0843163 | 12.78 | 0.0004* |
| Albumin_w6 | 4.52677405 | 1.4830029 | 9.32 | 0.0023* |
| Log[TNF_t4] | 5.8063819 | 1.3628655 | 16.92 | <.0001* |
| Log[IFX Reported [µg/mL]_t4] | -3.3239139 | 0.7572974 | 19.26 | <.0001* |
| Log[CRP_w14] | -0.8176145 | 0.3610735 | 5.13 | 0.0235* |

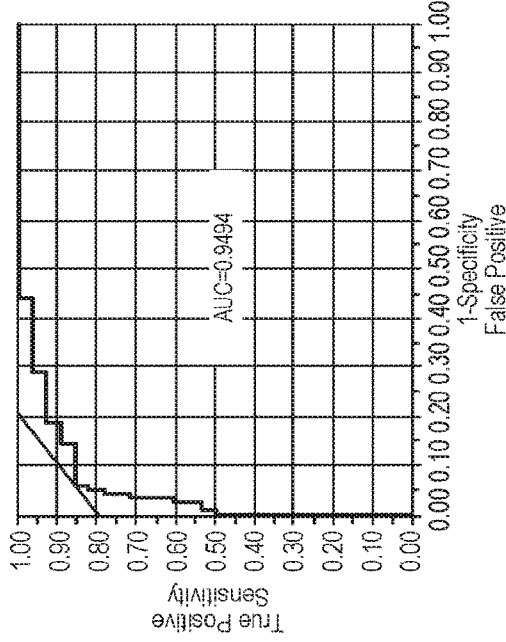

| RSquare (U) | 0.5729 |
|---|---|
| AICc | 80.2857 |
| BIC | 105.815 |
| Observations (or Sum Wgts) | 146 |

FIG. 15

| Initial Variables |
|---|
| TNF_T1 |
| CRP_w0 (mg/L) |
| Albumin_w0 (g/dL) |
| IMM use during IFX induction |
| Gender |
| Age |
| Age at diagnosis |
| BMI at 1st IFX |
| Hb at 1st IFX |
| Age at 1st IFX |
| Surgery previous |
| TNF_2, IFX Reported [μg/mL]_t2 |
| Total ATI Reported [U/mL]_T2[Detectable] |
| CRP_w2 |
| Albumin_w2 |
| TNF3, IFX Reported [μg/mL]_T3 |
| Total ATI Reported [U/mL]_T3 |
| CRP_w6 |
| Albumin_w6 |
| TNF4, IFX Reported [μg/mL]_t4 |
| CRP_w14 |
| Albumin_w14 |

| Model | -LogLikelihood | DF | ChiSquare | Prob>ChiSq |
|---|---|---|---|---|
| Difference | 38.440283 | 7 | 76.88057 | <.0001* |
| Full | 32.923772 | | | |
| Reduced | 71.364055 | | | |

| Parameter estimates | Estimate | Std Error | ChiSquare | Prob>ChiSq |
|---|---|---|---|---|
| Intercept | -29.438702 | 8.092877 | 13.23 | 0.0003* |
| Log[CRP_w0 (mg/L)] | 0.81506766 | 0.2881638 | 8.00 | 0.0047* |
| Sex [Male=1, Female=0][1] | -1.6318023 | 0.4693949 | 12.09 | 0.0005* |
| Hb at 1st IFX | 0.57087543 | 0.2633382 | 4.70 | 0.0302* |
| Albumin_w6 | 4.79053004 | 1.4625748 | 10.73 | 0.0011* |
| Log[CRP_w14] | -0.7859082 | 0.3411663 | 5.31 | 0.0212* |
| Log[TNF_t2] | -2.4981873 | 0.713716 | 12.25 | 0.0005* |
| Log[TNF4/IFX4] | 3.55503324 | 0.7153781 | 24.70 | <.0001* |

| | |
|---|---|
| RSquare (U) | 0.5387 |
| AICc | 82.8986 |
| BIC | 105.716 |
| Observations (or Sum Wgts) | 146 |

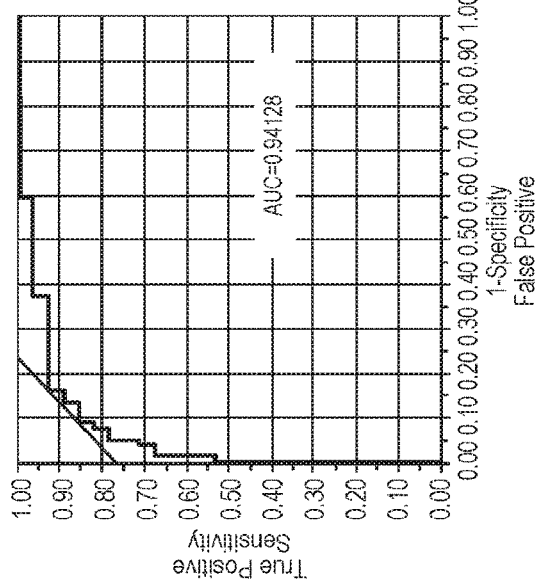

FIG. 16

| Marker 1 | Marker 2 | Estimate | P-value | R-Square | Direction |
|---|---|---|---|---|---|
| TNFa T1 | IFX T2 | -0.22 | 0.056 | 0.013 | Inverse |
| TNFa T1 | IFX T3 | -0.089 | 0.197 | | |
| TNFa T1 | IFX T4 | -0.16 | 0.009 | 0.032 | Inverse |

FIG. 18

| Var 1 | Var 2 | Mono Therapy (p-value) | Combination Therapy(P-value) |
|---|---|---|---|
| TNF T1 | IFX week2 | 0.48 | 0.067 |
| TNF T1 | IFX week6 | 0.53 | 0.24 |
| TNF T1 | IFX week 14 | 0.036 | 0.13 |

FIG. 19

| Time | | | Estimate | P-value | R-Square | Direction |
|---|---|---|---|---|---|---|
| baseline | HSA | TNF | -1.716 | 0.0007 | 0.052 | → |
| Week 2 | HSA | TNF | -1.135 | 0.0322 | 0.0189 | → |
| Week 6 | HSA | TNF | -1.39 | 0.0112 | 0.028 | → |
| Week 14 | HSA | TNF | -0.4588 | 0.529 | | |
| | HSA at week 14 | TNF baseline | -0.010 | 0.2491 | | |

FIG. 20

| Time | Var 1 | Var 2 | estimate | P value | R-Square | Direction |
|---|---|---|---|---|---|---|
| baseline | CRP | TNFa | 0.478 | 0.0001 | 0.068 | ↑ |
| Week 2 | CRP | TNFa | 0.06 | 0.1346 | | |
| Week 6 | CRP | TNFa | 0.085 | 0.0549 | 0.0137 | |
| Week 14 | CRP | TNFa | 0.059 | 0.2471 | | |
| | CRP week 14 | TNF a baseline | 0.0134 | 0.3356 | | |

FIG. 21

| Marker 1 | Marker 2 | Estimate | P-value | R-Square | Direction |
|---|---|---|---|---|---|
| CRP week 14 | TNFa/IFX (week2) | 0.025 | 0.0478 | 0.016 | ↑ |
| | TNFa/IFX (week 6) | 0.0245 | 0.0084 | 0.03 | ↑ |
| | TNFa/IFX (week 14) | 0.0347 | <0.0001 | 0.086 | ↑ |
| CRP at week 6 | TNFa/IFX week 2 | 0.088 | 0.3668 | | |

FIG. 22

| Var 1 | Var 2 | Mono Therapy (p-value) | Combination Therapy (p-value) |
|---|---|---|---|
| TNF T1/IFX T2 | CRP week 14 | 0.51 | 0.1 |
| TNF T1/IFX T3 | CRP week 14 | 0.36 | 0.0383 |
| TNF T1/IFX T4 | CRP week 14 | 0.15 | 0.0002 |

FIG. 23

| Var 1 | Var 2 | Mono Therapy (p-value) | Combination Therapy (p-value) |
|---|---|---|---|
| TNF/IFX T2 | CRP week 14 | 0.88 | 0.22 |
| TNF/IFX T3 | CRP week 14 | 0.1171 | 0.13 |
| TNF/IFX T4 | CRP week 14 | 0.1289 | 0.0004 |

*FIG. 24*

| Var 1 | Var 2 | Mono therapy (p-value) | Combination Therapy (p-value) |
|---|---|---|---|
| TNF/IFX T2 | ATI week 14 | 0.55 | 0.71 |
| TNF/IFX T3 | ATI week 14 | 0.0264 | 0.1026 |
| TNF/IFX T4 | ATI week 14 | 0.0071 | 0.0002 |
| TNF 1 | ATI week 14 | 0.45 | 0.42 |

FIG. 25

| Marker 1 | Marker 2 | Estimate | P-value | R-Square | Direction |
|---|---|---|---|---|---|
| CRP week 14 | IFX (week 2) | -0.603 | 0.014 | 0.027 | Inverse |
| | IFX (week 6) | -0.39 | 0.0079 | 0.031 | Inverse |
| | IFX (week 14) | -0.54 | <0.0001 | 0.09 | Inverse |
| CRP at week 6 | IFX at week 2 | -0.363 | 0.0643 | 0.0134 | Inverse |

*FIG. 26*

| Marker 1 | Marker 2 | Estimate | P-value | R-square | Direction |
|---|---|---|---|---|---|
| Baseline HSA | IFX (week 2) | 1.83 | <0.0001 | 0.165 | ↑ |
| Baseline HSA | IFX (week 6) | 2.54 | <0.0001 | 0.126 | ↑ |
| Baseline HSA | IFX (week 14) | 2.74 | <0.0001 | 0.1 | ↑ |

FIG. 27

| Time | Var 1 | Var 2 | Estimate | P-value | R-square | Direction |
|---|---|---|---|---|---|---|
| Baseline | CRP | HSA | -5.59 | <0.0001 | 0.18 | Inverse |
| Week2 | CRP | HSA | -4.927 | <0.0001 | 0.168 | Inverse |
| Week6 | CRP | HSA | -5.167 | <0.0001 | 0.169 | Inverse |
| Week14 | CRP | HSA | -5.715 | <0.0001 | 0.159 | Inverse |
| | CRP at week 14 | HSA baseline | -3.16 | 0.0003 | 0.067 | Inverse |

FIG. 28

Nominal Logistic Fit for Total ATI [U/mL]_T9

Whole Model Test

| Model | -LogLikelihood | DF | ChiSquare | Prob>ChiSq |
|---|---|---|---|---|
| Difference | 12.504089 | 2 | 25.00818 | <.0001* |
| Full | 5.13553e-7 | | | |
| Reduced | 12.504090 | | | |

| | |
|---|---|
| RSquare (U) | 1.0000 |
| AICc | 7.6 |
| BIC | 8.83332 |
| Observations (or Sum Wgts) | 19 |

Confusion Matrix

| | Detectable | Not detectable |
|---|---|---|
| Detectable | 7 | 0 |
| Not Detectable | 0 | 12 |

Effect Likelihood Ratio Tests

| Source | Nparm | DF | L-R ChiSquare | Prob>ChiSq |
|---|---|---|---|---|
| Log[IL-8(pg/mL]_T5] | 1 | 1 | 11.8867611 | 0.0006* |
| Log[IFX Reported [µg/mL]_T0] | 1 | 1 | 13.9583997 | 0.0002* |

*FIG. 36*

METHODS FOR PREDICTION OF ANTI-TNF α DRUG LEVELS AND AUTOANTIBODY FORMATION

CROSS-REFERENCES TO RELATED APPLICATIONS

This application is a continuation of U.S. application Ser. No. 15/486,072 filed Apr. 12, 2017, which is a continuation of International Application No. PCT/M2015/058048 filed Oct. 19, 2015, which claims priority to U.S. Provisional Application No. 62/065,997, filed Oct. 20, 2014, and U.S. Provisional Application No. 62/086,103, filed Dec. 1, 2014, the disclosures of which are hereby incorporated by reference in their entirety for all purposes.

BACKGROUND OF THE INVENTION

Tumor necrosis factor alpha (TNF-α) is a cytokine produced by numerous cell types, including monocytes and macrophages, that was originally identified based on its ability to induce the necrosis of certain mouse tumors. TNF-α has been implicated in the pathophysiology of a variety of other human diseases and disorders, including shock, sepsis, infections, autoimmune diseases, rheumatoid arthritis, Crohn's disease, transplant rejection, and graft-versus-host disease.

Because of the harmful role of TNF-α in a variety of human diseases and disorders, therapeutic strategies have been designed to inhibit or counteract TNF-α activity. Antibodies that bind to, and neutralize, TNF-α have been sought as a means to inhibit TNF-α activity. In particular, biological therapies have been applied to the treatment of inflammatory disorders such as Crohn's disease and autoimmune disorders such as rheumatoid arthritis. Examples of TNF-α inhibitors include REMICADE™ (infliximab), ENBREL™ (etanercept), HUMIRA™ (adalimumab), and CIMZIA™ (certolizumab pegol). While such biological therapies have demonstrated success in the treatment of Crohn's disease and rheumatoid arthritis, not all subjects treated respond, or respond well, to such therapy. Moreover, the administration of TNF-α inhibitors can induce an immune response to the drug and lead to the production of autoantibodies such as human anti-chimeric antibodies (HACA), human anti-humanized antibodies (HAHA), and human anti-mouse antibodies (HAMA). Such HACA, HAHA, or HAMA immune responses can be associated with hypersensitive reactions and dramatic changes in pharmacokinetics and biodistribution of the immunotherapeutic TNF-α inhibitor that preclude further treatment with the drug. Thus, there is a need in the art for selecting a therapeutic regimen with TNF-α inhibitors that is both efficacious and reduces the risk of autoantibody formation to the drug, thereby improving patient outcomes. The present invention satisfies this need and provides related advantages as well.

BRIEF SUMMARY OF THE INVENTION

In some aspects, the present invention provides methods for predicting whether a subject will develop autoantibodies to an anti-TNFα drug during the course of anti-TNFα drug therapy. In other aspects, the present invention provides methods for predicting the level of an anti-TNFα drug in a subject during the course of anti-TNFα drug therapy. Systems for predicting anti-TNFα drug levels and the likelihood of autoantibody formation during the course of anti-TNFα drug therapy are also provided herein. The present invention further provides methods for predicting a clinical outcome (e.g., endoscopic response) of a subject on anti-TNFα drug therapy.

In one aspect, the present invention provides a method for predicting whether a subject will develop autoantibodies to an anti-TNFα drug at a later time point during a course of therapy with the anti-TNFα drug, the method comprising measuring the level of the anti-TNFα drug in a sample obtained from the subject at an earlier time point during the course of therapy.

In another aspect, the present invention provides a method for predicting the level of an anti-TNFα drug in a subject at a later time point during a course of therapy with the anti-TNFα drug, the method comprising determining one or more predictor variables for the subject at an earlier time point during the course of therapy and/or prior to the initiation of the course of therapy.

In yet another aspect, the present invention provides a method for predicting whether a subject will develop autoantibodies to an anti-TNFα drug at a later time point during a course of therapy with the anti-TNFα drug, the method comprising determining one or more predictor variables for the subject at an earlier time point during the course of therapy and/or prior to the initiation of the course of therapy.

In an additional aspect, the present invention provides a system for predicting the level of an anti-TNFα drug in a subject at a later time point during a course of therapy with the anti-TNFα drug, the system comprising:
  (a) a data acquisition module configured to produce a data set comprising one or more predictor variables for the subject determined at an earlier time point during the course of therapy and/or prior to the initiation of the course of therapy;
  (b) a data processing module configured to process the data set by applying a statistical analysis to the data set to produce a statistically derived decision predicting the level of the anti-TNFα drug based upon the one or more predictor variables; and
  (c) a display module configured to display the statistically derived decision.

In a further aspect, the present invention provides a system for predicting whether a subject will develop autoantibodies to an anti-TNFα drug at a later time point during a course of therapy with the anti-TNFα drug, the system comprising:
  (a) a data acquisition module configured to produce a data set comprising one or more predictor variables for the subject determined at an earlier time point during the course of therapy and/or prior to the initiation of the course of therapy;
  (b) a data processing module configured to process the data set by applying a statistical analysis to the data set to produce a statistically derived decision predicting whether the subject will develop autoantibodies to the anti-TNFα drug based upon the one or more predictor variables; and
  (c) a display module configured to display the statistically derived decision.

In another aspect, the present invention provides a method for predicting a clinical outcome of a subject at a later time point during a course of therapy with the anti-TNFα drug, the method comprising determining one or more predictor variables selected from the level of IL12p40, the level of IL-8, the level of the anti-TNFα drug, and combinations thereof in a sample obtained from the subject at an earlier time point during the course of therapy.

In yet another aspect, the present invention provides a method for predicting whether a subject will develop autoantibodies to an anti-TNFα drug at a later time point during a course of therapy with the anti-TNFα drug, the method comprising determining one or more predictor variables selected from the level of IL-8, the level of the anti-TNF drug, the TNFα/drug ratio, and combinations thereof in a sample obtained from the subject at an earlier time point during the course of therapy.

Other objects, features, and advantages of the present invention will be apparent to one of skill in the art from the following detailed description and figures.

BRIEF DESCRIPTION OF THE DRAWINGS

FIG. 2 shows the association between TNFα, IFX, C-reactive protein (CRP), and human serum albumin (HSA) with ATI formation (p-values) at baseline (week 0), and at weeks 2, 6, and 14 following IFX therapy.

FIG. 3 shows a stratified analysis of the association between IFX levels and ATI formation in CD patients receiving IFX monotherapy or combination therapy with IFX and an immunosuppressive agent.

FIG. 5 shows the results of a quartile analysis that was performed to further characterize the association between IFX levels at week 6 and ATI formation at week 14.

FIG. 6 shows the results of a quartile analysis that was performed to further characterize the association between IFX levels at week 14 and ATI formation at week 14.

FIG. 7 shows the results of multiple regression modelling to predict IFX levels at week 14 using baseline measures of initial predictor variables.

FIG. 8 shows the results of multiple regression modelling to predict IFX levels at week 2 using baseline measures of initial predictor variables.

FIG. 9 shows the results of multiple regression modelling to predict IFX levels at week 6 using baseline and week 2 measures of initial predictor variables.

FIG. 10 shows the results of multiple regression modelling to predict IFX levels at week 14 using baseline, week 2, and week 6 measures of initial predictor variables.

FIG. 11 shows the results of multiple regression modelling to predict IFX levels at week 14 using baseline, week 2, and week 6 measures of initial predictor variables, but enforcing TNFα in the model.

FIG. 12 shows the results of multiple logistic regression modelling to predict ATI formation at week 14 using baseline measures of initial predictor variables.

FIG. 13 shows the results of multiple logistic regression modelling to predict ATI formation at week 14 using baseline and week 2 measures of initial predictor variables.

FIG. 14 shows the results of multiple logistic regression modelling to predict ATI formation at week 14 using baseline, week 2, and week 6 measures of initial predictor variables.

FIG. 15 shows the results of multiple logistic regression modelling to predict ATI formation at week 14 using all time point measurements of initial predictor variables.

FIG. 16 shows the results of multiple logistic regression modelling to predict ATI formation at week 14 using all time point measurements of initial predictor variables including TNFα/IFX ratios.

FIG. 18 shows the association between TNFα levels at baseline and IFX levels at weeks 2, 6, and 14.

FIG. 19 shows a stratified analysis of the association between baseline TNFα levels and IFX levels in CD patients receiving IFX monotherapy or combination therapy with IFX and an immunosuppressive agent.

FIG. 20 shows the association between HSA levels and TNFα levels.

FIG. 21 shows the association between CRP levels and TNFα levels.

FIG. 22 shows the association between TNFα/IFX ratios and CRP levels.

FIG. 23 shows a stratified analysis of the association between ratios of baseline TNFα levels to IFX levels at different time points and CRP levels at week 14 in CD patients receiving IFX monotherapy or combination therapy with IFX and an immunosuppressive agent.

FIG. 24 shows a stratified analysis of the association between ratios of TNFα levels to IFX levels at different time points and CRP levels at week 14 in CD patients receiving IFX monotherapy or combination therapy with IFX and an immunosuppressive agent.

FIG. 25 shows a stratified analysis of the association between ratios of TNFα levels to IFX levels at different time points and ATI formation at week 14 in CD patients receiving IFX monotherapy or combination therapy with IFX and an immunosuppressive agent.

FIG. 26 shows the association between IFX levels and CRP levels.

FIG. 27 shows the association between baseline HSA levels and IFX levels during the course of therapy.

FIG. 28 shows the association between CRP levels and HSA levels at baseline and at different time points during the course of therapy.

FIG. 36 shows the results of multiple regression modelling using IL-8 levels together with IFX levels to predict ATI formation at T9 (i.e., by week 6 or within the first 6 weeks of IFX therapy).

DETAILED DESCRIPTION OF THE INVENTION

I. Introduction

Figure 1A:
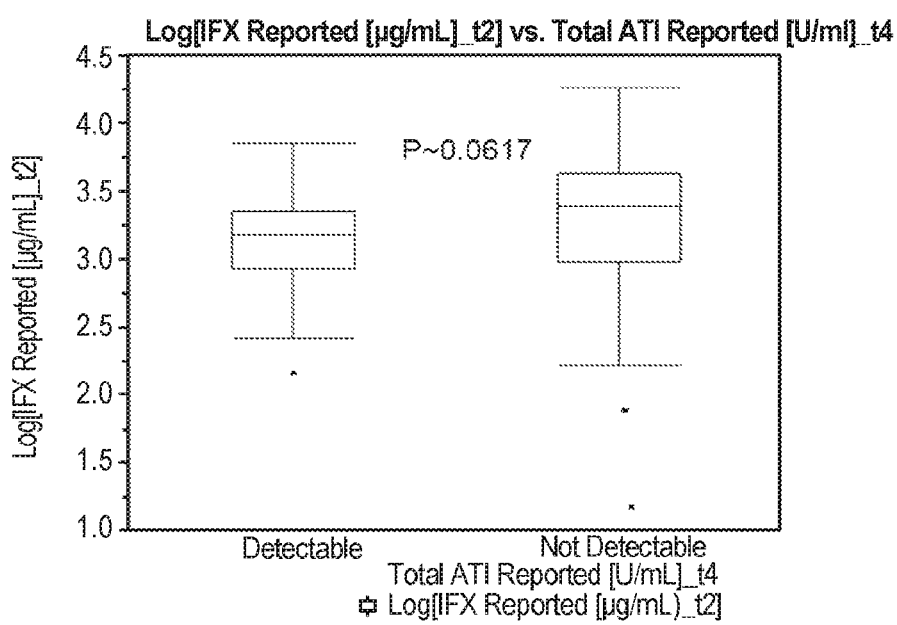
FIGS. 1A-1C show the relationship between IFX levels and the ATI formation in CD patients at week 2 (FIG. 1A), week 6 (FIG. 1B), and week 14 (FIG. 1C) following the initiation of IFX therapy (baseline or week 0).

The present invention provides methods for predicting whether a subject will develop autoantibodies to an anti-TNFα drug during the course of anti-TNFα drug therapy. The present invention also provides methods for predicting the level of an anti-TNFα drug in a subject during the course of anti-TNFα drug therapy. The present invention further provides systems for predicting anti-TNFα drug levels and the likelihood of autoantibody formation during the course of anti-TNFα drug therapy. The present invention also provides methods for predicting a clinical outcome (e.g., endoscopic response) of a subject on anti-TNFα drug therapy.

In certain aspects, the examples described herein demonstrate that the level of an anti-TNFα drug (e.g., IFX) at an earlier time point during therapy is predictive of anti-TNFα drug autoantibody (e.g., ATI) formation at a later time point during therapy. In other aspects, the examples described herein demonstrate that anti-TNFα drug (e.g., IFX) levels above a specific reference level or cut-off value (i.e., drug levels in the $4^{th}$ quartile or Q4 based on quartile analysis) at an earlier time point during therapy is predictive of whether a patient will develop anti-TNFα drug autoantibody (e.g., ATI) at a later time point during therapy.

In certain aspects, the examples described herein demonstrate that the initial dose of an anti-TNFα drug (e.g., IFX) can be individualized and tailored for each patient at the start of therapy based on the use of predictive models such as multiple regression models. In other aspects, the examples described herein demonstrate that patients predicted to develop anti-TNFα drug autoantibody (e.g., ATI) during the course of anti-TNFα drug (e.g., IFX) therapy based on the use of predictive models can be administered an initial dose of the drug that is increased compared to the normal starting dose and/or an increased dose of an immunosuppressive agent such as azathioprine (AZA), 6-mercaptopurine (6-MP), or methotrexate (MTX).

In certain aspects, the examples described herein demonstrate that biomarkers such as IL12p40, IL-8, and anti-TNFα drug (e.g., IFX) at one or more earlier time points during the course of anti-TNFα drug (e.g., IFX) therapy are predictive of clinical outcome (e.g., endoscopic response) at a later time point during therapy. In certain embodiments, the level of IL12p40 and/or IL-8 at week 2 can be used to predict clinical outcome (e.g., endoscopic response) at week 8 of anti-TNFα drug (e.g., IFX) therapy. In other embodiments, the level of IFX at 24 hours after dosing can be used to predict clinical outcome (e.g., endoscopic response) at week 8 of anti-TNFα drug (e.g., IFX) therapy. In other aspects, the examples described herein demonstrate that biomarkers such as IL-8 and anti-TNFα drug (e.g., IFX) as well as a ratio of TNFα to anti-TNFα drug (e.g., IFX) at one or more earlier time points during the course of anti-TNFα drug (e.g., IFX) therapy are predictive of anti-TNFα drug autoantibody (e.g., ATI) formation at a later time point during therapy. In certain embodiments, the level of IL-8 at week 2, the level of IFX at 24 hours after dosing, and/or the ratio of TNFα level to IFX level (i.e., TNFα/IFX ratio) at 24 hours after dosing can be used to predict anti-TNFα drug autoantibody (e.g., ATI) formation at week 6 of anti-TNFα drug (e.g., IFX) therapy (i.e., by week 6 or within the first 6 weeks of therapy).

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "course of therapy" includes any therapeutic approach taken to relieve or prevent one or more symptoms associated with a TNFα-mediated disease or disorder. The term encompasses administering any compound, drug, procedure, and/or regimen useful for improving the health of an individual with a TNFα-mediated disease or disorder and includes any of the therapeutic agents described herein. One skilled in the art will appreciate that either the course of therapy or the dose of the current course of therapy can be changed (e.g., increased or decreased) using the methods and systems of the present invention.

The term "TNFα" is intended to include a human cytokine that exists as a 17 kDa secreted form and a 26 kDa membrane associated form, the biologically active form of which is composed of a trimer of noncovalently bound 17 kDa molecules. The structure of TNFα is described further in, for example, Jones et al., *Nature,* 338:225-228 (1989). The term TNFα is intended to include human TNFα, a recombinant human TNFα (rhTNF-α), or TNFα that is at least about 80% identity to the human TNFα protein. Human TNFα consists of a 35 amino acid (aa) cytoplasmic domain, a 21 aa transmembrane segment, and a 177 aa extracellular domain (ECD) (Pennica, D. et al. (1984) *Nature* 312:724). Within the ECD, human TNFα shares 97% aa sequence identity with rhesus TNFα, and 71% to 92% aa sequence identity with bovine, canine, cotton rat, equine, feline, mouse, porcine, and rat TNFα. TNFα can be prepared by standard recombinant expression methods or purchased commercially (R & D Systems, Catalog No. 210-TA, Minneapolis, Minn.).

In certain embodiments, "TNFα" is an "antigen," which includes a molecule or a portion of the molecule capable of being bound by an anti-TNF-α drug. TNFα can have one or more than one epitope. In certain instances, TNFα will react, in a highly selective manner, with an anti-TNFα antibody. Preferred antigens that bind antibodies, fragments, and regions of anti-TNFα antibodies include at least 5 amino acids of human TNFα. In certain instances, TNFα is a sufficient length having an epitope of TNFα that is capable of binding anti-TNFα antibodies, fragments, and regions thereof.

The terms "anti-TNFα drug" or "TNFα inhibitor" as used herein are intended to encompass agents including proteins, antibodies, antibody fragments, fusion proteins (e.g., Ig fusion proteins or Fc fusion proteins), multivalent binding proteins (e.g., DVD Ig), small molecule TNFα antagonists and similar naturally- or nonnaturally-occurring molecules, and/or recombinant and/or engineered forms thereof, that, directly or indirectly, inhibits TNFα activity, such as by inhibiting interaction of TNFα with a cell surface receptor for TNFα, inhibiting TNFα protein production, inhibiting TNFα gene expression, inhibiting TNFα secretion from cells, inhibiting TNFα receptor signaling or any other means resulting in decreased TNF-α activity in a subject. The term "anti-TNFα drug" or "TNFα inhibitor" preferably includes agents which interfere with TNFα activity. Examples of anti-TNF drugs include, without limitation, infliximab (REMICADE™, Johnson and Johnson), human anti-TNF monoclonal antibody adalimumab (D2E7/HUMIRA™, Abbott Laboratories), etanercept (ENBREL™, Amgen), human anti-TNF monoclonal antibody golimumab (SIMPONI®, CNTO 148), CDP 571 (Celltech), and pegylated Fab' fragment of a humanized TNF inhibitor monoclonal antibody (certolizumab pegol (CIMZIA®, UCB, Inc.), as well as other compounds which inhibit TNF activity, such that when administered to a subject suffering from or at risk of suffering from a disorder in which TNFα activity is detrimental (e.g., IBD or clinical subtype thereof such as CD), the disorder is treated.

The terms "anti-drug antibody" and "ADA" are intended to encompass a human anti-chimeric antibody (HACA), a human anti-humanized antibody (HAHA), and a human anti-mouse antibody (HAMA). The terms "antibodies to infliximab" and "ATI" refer to antibodies against the anti-TNFα antibody drug infliximab.

The term "co-administer" includes to administer more than one active agent, such that the duration of physiological effect of one active agent overlaps with the physiological effect of a second active agent.

The term "subject," "patient," or "individual" typically includes humans, but also includes other animals such as, e.g., other primates, rodents, canines, felines, equines, ovines, porcines, and the like.

As used herein, the terms "immunosuppressive drug," "immunosuppressive agent," and "immunomodulator" include any substance capable of producing an immunosuppressive effect, e.g., the prevention or diminution of the immune response, as by irradiation or by administration or co-administration of drugs or agents such as anti-metabolites, anti-folates, thiopurine drugs, anti-lymphocyte sera, antibodies, etc. Non-limiting examples of immunosuppressive drugs include anti-folates (e.g., methotrexate (MTX)), thiopurine drugs (e.g., azathioprine (AZA)), sirolimus (rapamycin), temsirolimus (Torisel®), everolimus (Afinitor®), tacrolimus (FK-506), FK-778, anti-lymphocyte globulin antibodies, anti-thymocyte globulin antibodies, anti-CD3 antibodies, anti-CD4 antibodies, antibody-toxin conjugates, cyclosporine, mycophenolate, mizoribine monophosphate, scoparone, glatiramer acetate, pharmaceutically acceptable salts thereof, metabolites thereof, derivatives thereof, prodrugs thereof, and combinations thereof.

The term "thiopurine drug" includes azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof.

The term "sample" includes any biological specimen obtained from a subject. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), cellular extracts thereof, and an immunoglobulin enriched fraction derived from one or more of these bodily fluids or tissues. In some embodiments, the sample is whole blood, a fractional component thereof such as plasma, serum, or a cell pellet, or an immunoglobulin enriched fraction thereof. One skilled in the art will appreciate that samples such as serum samples can be diluted prior to the analysis. In certain embodiments, the sample is obtained by isolating PBMCs and/or PMN cells using any technique known in the art. In certain other embodiments, the sample is a tissue biopsy such as, e.g., from a site of inflammation such as a portion of the gastrointestinal tract.

In "quartile analysis", there are three numbers (values) that divide a range of data into four equal parts. The first quartile (also called the 'lower quartile') is the number below which lies the bottom 25 percent of the data. The second quartile (the 'median') divides the range in the middle and has 50 percent of the data below it. The third quartile (also called the 'upper quartile') has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

As used herein, the phrase "at a later time point" includes phrases such as "by a later time point" and "within the later time point." For example, a method for predicting whether a subject will develop autoantibodies to an anti-TNFα drug at a later time point during a course of therapy includes a method for predicting whether a subject will develop autoantibodies to an anti-TNFα drug by the later time point during the course of therapy as well as a method for predicting whether a subject will develop autoantibodies to an anti-TNFα drug within the later time point during the course of therapy.

The steps of the methods of the present invention do not necessarily have to be performed in the particular order in which they are presented. A person of ordinary skill in the art would understand that other orderings of the steps of the methods of the invention are encompassed within the scope of the present invention.

III. Description of the Embodiments

In some aspects, the present invention provides methods for predicting whether a subject will develop autoantibodies to an anti-TNFα drug during the course of anti-TNFα drug therapy. In other aspects, the present invention provides methods for predicting the level of an anti-TNFα drug in a subject during the course of anti-TNFα drug therapy. Systems for predicting anti-TNFα drug levels and the likelihood of autoantibody formation during the course of anti-TNFα drug therapy are also provided herein. The present invention further provides methods for predicting a clinical outcome (e.g., endoscopic response) of a subject on anti-TNFα drug therapy.

In one aspect, the present invention provides a method for predicting whether a subject will develop autoantibodies to an anti-TNFα drug at a later time point during a course of therapy with the anti-TNFα drug, the method comprising measuring the level of the anti-TNFα drug in a sample obtained from the subject at an earlier time point during the course of therapy.

In some embodiments, the subject has inflammatory bowel disease (IBD) or a clinical subtype thereof such as Crohn's disease (CD) or ulcerative colitis (UC). In other embodiments, the sample is a whole blood, serum, or plasma sample.

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In some embodiments, the autoantibodies to the anti-TNFα drug are human anti-chimeric antibodies (HACA), human anti-humanized antibodies (HAHA), human anti-mouse antibodies (HAMA), or combinations thereof.

In some embodiments, the earlier time point is at day 1, 2, 3, 4, 5, 6, 7, 8, 9, or 10, or at week 1, 2, 3, 4, 5, 6, 7, 8, 9, 10, 11, or 12 during the course of therapy. In certain embodiments, the earlier time point is at week 2 or week 6 during the course of therapy. In other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 14 during the course of therapy (e.g., by week 14 or within the first 14 weeks of therapy). In preferred embodiments, the earlier time point is at week 2 or week 6 during the course of therapy, and the later time point is at week 14 during the course of therapy.

In particular embodiments, the method further comprises comparing the measured level of the anti-TNFα drug to a reference level of the anti-TNFα drug. In certain instances, a reference level of the anti-TNFα drug can be established from IBD (e.g., CD) subjects on therapy with the drug. In some embodiments, the method predicts that the subject will not develop autoantibodies to the anti-TNFα drug at a later time point during the course of therapy when the measured level of the anti-TNFα drug is greater than or equal to the reference level of the anti-TNFα drug. In certain embodiments, the reference level corresponds to a mean level or a specific quartile level (e.g., Q1, Q2, Q3, Q4 obtained from quartile analysis) of the anti-TNFα drug from a dataset of samples from IBD (e.g., CD) subjects on therapy with the drug. For example, the reference level of the anti-TNFα drug can be the Q4 value from a dataset of a plurality of anti-TNFα drug assays using samples from IBD (e.g., CD) subjects on therapy with the drug. In preferred embodiments, the reference level is derived from quartile analysis of a reference database of samples from IBD (e.g., CD) subjects on anti-TNFα drug therapy and corresponds to the level of the anti-TNFα drug in the quartile that contains samples with the highest anti-TNFα drug levels (e.g., Q4).

As a non-limiting example, a subject is predicted not to develop autoantibodies to infliximab (ATI) at week 14 if the infliximab level at week 2 is greater than a reference level of about 37 µg/ml (i.e., the Q4 value). As another non-limiting example, a subject is predicted not to develop ATI at week 14 if the infliximab level at week 6 is greater than a reference level of about 35 µg/ml (i.e., the Q4 value). As yet another non-limiting example, a subject is predicted not to develop ATI at week 14 if the infliximab level at week 14 is greater than a reference level of about 14 µg/ml (i.e., the Q4 value).

In another aspect, the present invention provides a method for predicting the level of an anti-TNFα drug in a subject at a later time point during a course of therapy with the anti-TNFα drug, the method comprising determining one or more predictor variables for the subject at an earlier time point during the course of therapy and/or prior to the initiation of the course of therapy.

In some embodiments, the subject has inflammatory bowel disease (IBD) or a clinical subtype thereof such as Crohn's disease (CD) or ulcerative colitis (UC).

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In some embodiments, the one or more predictor variables comprises at least 1, 2, 3, 4, 5, 6, 7, 8, 9, 10, 11, 12, 13, 14, 15, 16, 17, 18, 19, 20, or more predictor variables. In certain embodiments, the one or more predictor variables is selected from the group consisting of TNFα level, anti-TNFα drug level, C-reactive protein (CRP) level, human serum albumin (HSA) level, immunomodulator (IMM) use, gender, age, age at diagnosis, Body Mass Index (BMI) at first drug dose, hemoglobin (Hb) level at first drug dose, age at first drug dose (years), surgery previous to first drug dose, ratio of TNFα level to drug level, presence of autoantibodies to the drug, and combinations thereof.

In certain instances, the one or more predictor variables is determined prior to the initiation of the course of therapy. In certain other instances, the one or more predictor variables is determined prior to the initiation of the course of therapy and at one or more times during the course of therapy.

In some embodiments, the method comprises determining the one or more predictor variables prior to the initiation of the course of therapy (i.e., baseline values) to predict the level of the anti-TNFα drug at a later time point during the course of therapy. As a non-limiting example, baseline values (i.e., at week 0) of a combination of the predictor variables TNFα (e.g., Log[TNFα]), albumin, age, and BMI are determined to predict the level of infliximab (IFX) at a later time during the course of therapy (e.g., at week 14). As another non-limiting example, baseline values (i.e., at week 0) of a combination of the predictor variables CRP (e.g., Log[CRP]), albumin, gender, and BMI are determined to predict the level of IFX at a later time during the course of therapy (e.g., at week 2).

In other embodiments, the method comprises determining the one or more predictor variables prior to the initiation of the course of therapy and at one or more times during the course of therapy to predict the level of the anti-TNFα drug at a later time point during the course of therapy. As a non-limiting example, baseline values (i.e., at week 0) of a combination of the predictor variables IMM use during IFX induction and previous surgery and week 2 values of IFX (e.g., Log[IFX]) and CRP (e.g., Log[CRP]) are determined to predict the level of IFX at a later time during the course of therapy (e.g., at week 6). As another non-limiting example, baseline values (i.e., at week 0) of the predictor variable age at 1st IFX (years), week 2 values of the predictor variable IFX (e.g., Log[IFX]), and week 6 values of a combination of the predictor variables IFX (e.g., Log [IFX]), total ATI, and CRP (e.g., Log[CRP]) are determined to predict the level of IFX at a later time during the course of therapy (e.g., at week 14). As yet another non-limiting example, baseline values (i.e., at week 0) of the predictor variable age at 1st IFX (years), week 2 values of the predictor variable IFX (e.g., Log[IFX]), and week 6 values of a combination of the predictor variables IFX (e.g., Log [IFX]), total ATI, TNFα (e.g., Log[TNFα]), and CRP (e.g., Log[CRP]) are determined to predict the level of IFX at a later time during the course of therapy (e.g., at week 14).

In some embodiments, the earlier time point or a plurality of one or more time points is at day 1, 2, 3, 4, 5, 6, 7, 8, 9, or 10, or at week 1, 2, 3, 4, 5, 6, 7, 8, 9, 10, 11, or 12, or any combination thereof, during the course of therapy. In certain embodiments, the earlier time point is at week 2 or week 6 during the course of therapy. In other embodiments, the plurality of one or more time points is at week 2 and week 6 during the course of therapy. In yet other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 2, week 6, or week 14 during the course of therapy. In preferred embodiments, the earlier time point is at week 2 or week 6 or a combination thereof during the course of therapy, and the later time point is at week 14 during the course of therapy.

In other embodiments, the method further comprises applying a statistical analysis on the one or more predictor variables. In particular embodiments, the statistical analysis comprises a multiple logistic regression model. In certain embodiments, an initial dose of the anti-TNFα drug is determined based upon the statistical analysis.

In yet another aspect, the present invention provides a method for predicting whether a subject will develop autoantibodies to an anti-TNFα drug at a later time point during a course of therapy with the anti-TNF drug, the method comprising determining one or more predictor variables for the subject at an earlier time point during the course of therapy and/or prior to the initiation of the course of therapy.

In some embodiments, the subject has inflammatory bowel disease (IBD) or a clinical subtype thereof such as Crohn's disease (CD) or ulcerative colitis (UC).

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In some embodiments, the autoantibodies to the anti-TNFα drug are human anti-chimeric antibodies (HACA), human anti-humanized antibodies (HAHA), human anti-mouse antibodies (HAMA), or combinations thereof.

In some embodiments, the one or more predictor variables comprises at least 1, 2, 3, 4, 5, 6, 7, 8, 9, 10, 11, 12, 13, 14, 15, 16, 17, 18, 19, 20, or more predictor variables. In certain embodiments, the one or more predictor variables is selected from the group consisting of TNFα level, anti-TNFα drug level, C-reactive protein (CRP) level, human serum albumin (HSA) level, immunomodulator (IMM) use, gender, age, age at diagnosis, Body Mass Index (BMI) at first drug dose, hemoglobin (Hb) level at first drug dose, age at first drug dose (years), surgery previous to first drug dose, ratio of TNFα level to drug level, presence of autoantibodies to the drug, and combinations thereof.

In certain instances, the one or more predictor variables is determined prior to the initiation of the course of therapy. In certain other instances, the one or more predictor variables is determined prior to the initiation of the course of therapy and at one or more times during the course of therapy.

In some embodiments, the method comprises determining the one or more predictor variables prior to the initiation of the course of therapy (i.e., baseline values) to predict whether the subject will develop autoantibodies to the anti-TNFα drug at a later time point during the course of therapy (e.g., by the later time point or within the later time point during therapy). As a non-limiting example, baseline values (i.e., at week 0) of a combination of the predictor variables TNFα (i.e., Log[TNFα]), gender, hemoglobin at 1st IFX, and IMM use during IFX induction are determined to predict ATI formation at a later time during the course of therapy (e.g., at week 14, by week 14, or within the first 14 weeks of therapy).

In other embodiments, the method comprises determining the one or more predictor variables prior to the initiation of the course of therapy and at one or more times during the course of therapy to predict whether the subject will develop autoantibodies to the anti-TNFα drug at a later time point during the course of therapy (e.g., by the later time point or within the later time point during therapy). As a non-limiting example, baseline values (i.e., at week 0) of a combination of the predictor variables TNFα (e.g., Log[TNFα ]), IMM use during IFX induction, gender, and hemoglobin at 1st IFX, and week 2 values of a combination of the predictor variables albumin and IFX (e.g., Log[IFX]) are determined to predict ATI formation at a later time during the course of therapy (e.g., at week 14, by week 14, or within the first 14 weeks of therapy). As another non-limiting example, baseline values (i.e., at week 0) of a combination of the predictor variables TNFα (e.g., Log[TNFα]), gender, and hemoglobin at 1st IFX, and week 6 values of a combination of the predictor variables albumin and IFX (e.g., Log[IFX]) are determined to predict ATI formation at a later time during the course of therapy (e.g., at week 14, by week 14, or within the first 14 weeks of therapy). As yet another non-limiting example, baseline values (i.e., at week 0) of a combination of the predictor variables CRP (e.g., Log[CRP]), gender, and hemoglobin at 1st IFX, week 2 values of the predictor variable TNFα (e.g., Log[TNFα]), week 6 values of the predictor variable albumin, and week 14 values of a combination of the predictor variables TNFα (e.g., Log[TNFα]), IFX (e.g., Log[IFX]), and CRP (e.g., Log[CRP]) are determined to predict ATI formation at a later time during the course of therapy (e.g., at week 14, by week 14, or within the first 14 weeks of therapy). As another non-limiting example, baseline values (i.e., at week 0) of a combination of the predictor variables CRP (e.g., Log[CRP]), gender, and hemoglobin at 1st IFX, week 2 values of the predictor variable TNFα (e.g., Log[TNFα]), week 6 values of the predictor variable albumin, and week 14 values of a combination of the predictor variables TNFα/IFX ratio (e.g., Log[TNFα/IFX]) and CRP (e.g., Log[CRP]) are determined to predict ATI formation at a later time during the course of therapy (e.g., at week 14, by week 14, or within the first 14 weeks of therapy).

In some embodiments, the earlier time point or a plurality of one or more time points is at day 1, 2, 3, 4, 5, 6, 7, 8, 9, or 10, or at week 1, 2, 3, 4, 5, 6, 7, 8, 9, 10, 11, or 12, or any combination thereof, during the course of therapy. In certain embodiments, the earlier time point is at week 2 or week 6 during the course of therapy. In other embodiments, the plurality of one or more time points is at week 2 and week 6 during the course of therapy. In yet other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 2, week 6, or week 14 during the course of therapy (e.g., by week 2, week 6, or week 14 or within the first 2 weeks, 6 weeks, or 14 weeks of therapy). In preferred embodiments, the earlier time point is at week 2, week 6, week 14, or a combination thereof during the course of therapy, and the later time point is at week 14 during the course of therapy (e.g., by week 14 or within the first or 14 weeks of therapy).

In other embodiments, the method further comprises applying a statistical analysis on the one or more predictor variables. In particular embodiments, the statistical analysis comprises a multiple logistic regression model. In certain embodiments, an initial dose of the anti-TNFα drug is determined based upon the statistical analysis. In some instances, the initial dose of the anti-TNFα drug is increased relative to a normal starting dose of the anti-TNFα drug if the subject is predicted to develop autoantibodies to the anti-TNFα drug. In other instances, the initial dose of the anti-TNFα drug further comprises an increased dose of an immunosuppressive agent.

In an additional aspect, the present invention provides a system for predicting the level of an anti-TNF drug in a subject at a later time point during a course of therapy with the anti-TNFα drug, the system comprising:
(a) a data acquisition module configured to produce a data set comprising one or more predictor variables for the subject determined at an earlier time point during the course of therapy and/or prior to the initiation of the course of therapy;
(b) a data processing module configured to process the data set by applying a statistical analysis to the data set to produce a statistically derived decision predicting the level of the anti-TNFα drug based upon the one or more predictor variables; and
(c) a display module configured to display the statistically derived decision.

In a further aspect, the present invention provides a system for predicting whether a subject will develop autoantibodies to an anti-TNFα drug at a later time point during a course of therapy with the anti-TNFα drug, the system comprising:
(a) a data acquisition module configured to produce a data set comprising one or more predictor variables for the subject determined at an earlier time point during the course of therapy and/or prior to the initiation of the course of therapy;
(b) a data processing module configured to process the data set by applying a statistical analysis to the data set to produce a statistically derived decision predicting whether the subject will develop autoantibodies to the anti-TNFα drug based upon the one or more predictor variables; and
(c) a display module configured to display the statistically derived decision.

In some embodiments, the subject has inflammatory bowel disease (IBD) or a clinical subtype thereof such as Crohn's disease (CD) or ulcerative colitis (UC).

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In some embodiments, the autoantibodies to the anti-TNFα drug are human anti-chimeric antibodies (HACA), human anti-humanized antibodies (HAHA), human anti-mouse antibodies (HAMA), or combinations thereof.

In some embodiments, the one or more predictor variables comprises at least 1, 2, 3, 4, 5, 6, 7, 8, 9, 10, 11, 12, 13, 14, 15, 16, 17, 18, 19, 20, or more predictor variables. In certain embodiments, the one or more predictor variables is selected from the group consisting of TNFα level, C-reactive protein (CRP) level, human serum albumin (HSA) level, immunomodulator (IMM) use, gender, age, age at diagnosis, Body Mass Index (BMI) at first drug dose, hemoglobin (Hb) level at first drug dose, age at first drug dose (years), surgery previous to first drug dose, ratio of TNFα level to drug level, presence of autoantibodies to the drug, and combinations thereof.

In certain instances, the one or more predictor variables is determined prior to the initiation of the course of therapy. In certain other instances, the one or more predictor variables is determined prior to the initiation of the course of therapy and at one or more times during the course of therapy.

In some embodiments, the earlier time point or a plurality of one or more time points is at day 1, 2, 3, 4, 5, 6, 7, 8, 9, or 10, or at week 1, 2, 3, 4, 5, 6, 7, 8, 9, 10, 11, or 12, or any combination thereof, during the course of therapy. In certain embodiments, the earlier time point is at week 2 or week 6 during the course of therapy. In other embodiments, the plurality of one or more time points is at week 2 and week 6 during the course of therapy. In yet other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 2, week 6, or week 14 during the course of therapy (e.g., by week 2, week 6, or week 14 or within the first 2 weeks, 6 weeks, or 14 weeks of therapy). In preferred embodiments, the earlier time point is at week 2, week 6, week 14, or a combination thereof during the course of therapy, and the later time point is at week 14 during the course of therapy (e.g., by week 14 or within the first or 14 weeks of therapy).

In particular embodiments, the statistical analysis comprises a multiple logistic regression model. In certain embodiments, an initial dose of the anti-TNFα a drug is determined based upon the statistically derived decision.

In another aspect, the present invention provides a method for predicting a clinical outcome of a subject at a later time point during a course of therapy with the anti-TNFα drug, the method comprising determining one or more predictor variables selected from the level of IL12p40, the level of IL-8, the level of the anti-TNFα drug, and combinations thereof in a sample obtained from the subject at an earlier time point during the course of therapy.

In some embodiments, the subject has inflammatory bowel disease (IBD) or a clinical subtype thereof such as Crohn's disease (CD) or ulcerative colitis (UC). In other embodiments, the sample is a whole blood, serum, or plasma sample.

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In certain embodiments, the clinical outcome corresponds to an endoscopic response at week 8 during the course of therapy. In other embodiments, the method comprises measuring the level of IL12p40 and the level of IL-8 in the sample.

In some embodiments, the earlier time point is at day 1, 2, 3, 4, 5, 6, 7, 8, 9, or 10, or at week 1, 2, 3, 4, 5, 6, 7, 8, 9, 10, 11, or 12 during the course of therapy. In certain embodiments, the earlier time point is at 24 hours after dosing or at week 2 during the course of therapy. In other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 8 during the course of therapy (e.g., by week 8 or within the first 8 weeks of therapy). In preferred embodiments, the earlier time point is at 24 hours after dosing or at week 2 during the course of therapy, and the later time point is at week 8 during the course of therapy.

In particular embodiments, the method further comprises comparing the measured level of the one or more predictor variables to a reference level of the one or more predictor variables. In certain instances, a reference level of the one or more predictor variables can be established from IBD (e.g., UC) subjects on therapy with the drug who have responded to the drug (i.e., "responders"). In some embodiments, the method predicts that the subject will or will not have an endoscopic response at a later time point during the course of therapy when the measured level of the predictor variable is less than, greater than, or equal to the reference level of the predictor variable.

As a non-limiting example, a subject is predicted not to have an endoscopic response at week 8 if the level of IL12p40 at week 2 is greater than a reference level of IL12p40 (e.g., the level of IL12p40 in a sample from a responder at week 2). As another non-limiting example, a subject is predicted not to have an endoscopic response at week 8 if the level of IL-8 at week 2 is greater than a reference level of IL12p40 (e.g., the level of IL12p40 in a sample from a responder at week 2). As yet another non-limiting example, a subject is predicted not to have an endoscopic response at week 8 if the level of anti-TNFα drug (e.g., IFX) at 24 hours after dosing is lower than a reference level of the anti-TNFα drug (e.g., the level of the anti-TNFα drug in a sample from a responder at 24 hours after dosing).

In other embodiments, the method further comprises applying a statistical analysis on the one or more predictor variables. In particular embodiments, the statistical analysis comprises a multiple logistic regression model. In certain embodiments, a clinical outcome at the later time point is predicted based upon the statistical analysis.

In yet another aspect, the present invention provides a method for predicting whether a subject will develop autoantibodies to an anti-TNFα drug at a later time point during a course of therapy with the anti-TNFα drug, the method comprising determining one or more predictor variables selected from the level of IL-8, the level of the anti-TNFα drug, the TNFα/drug ratio, and combinations thereof in a sample obtained from the subject at an earlier time point during the course of therapy.

In some embodiments, the subject has inflammatory bowel disease (IBD) or a clinical subtype thereof such as Crohn's disease (CD) or ulcerative colitis (UC). In other embodiments, the sample is a whole blood, serum, or plasma sample.

In some embodiments, the course of therapy is monotherapy with the anti-TNFα drug. In other embodiments, the course of therapy is combination therapy with the anti-TNFα drug and an immunosuppressive agent. Non-limiting examples of immunosuppressive agents include anti-metabolites, e.g., methotrexate (MTX) and other anti-folates, thiopurine drugs such as azathioprine (AZA) and 6-mercaptopurine (6-MP), and combinations thereof.

In certain embodiments, the anti-TNFα drug is selected from the group consisting of REMICADE™ (infliximab), ENBREL® (etanercept), HUMIRA® (adalimumab), CIMZIA® (certolizumab pegol), SIMPONI® (golimumab), and combinations thereof.

In some embodiments, the autoantibodies to the anti-TNFα drug are human anti-chimeric antibodies (HACA), human anti-humanized antibodies (HAHA), human anti-mouse antibodies (HAMA), or combinations thereof.

In certain embodiments, the method comprises measuring the level of IL-8 and the level of the anti-TNFα drug in the sample. In other embodiments, the method comprises measuring the level of IL-8 and the TNFα/drug ratio in the sample.

In some embodiments, the earlier time point is at day 1, 2, 3, 4, 5, 6, 7, 8, 9, or 10, or at week 1, 2, 3, 4, 5, 6, 7, 8, 9, 10, 11, or 12 during the course of therapy. In certain embodiments, the earlier time point is at 24 hours after dosing or at week 2 during the course of therapy. In other embodiments, the later time point is at week 2, 3, 4, 5, 6, 7, 8, 9, 10, 11, 12, 13, 14, 15, 16, 17, 18, 19, 20, 21, 22, 23, 24, or 25 during the course of therapy. In certain embodiments, the later time point is at week 6 during the course of therapy (e.g., by week 6 or within the first 6 weeks of therapy). In preferred embodiments, the earlier time point is at 24 hours after dosing or at week 2 during the course of therapy, and the later time point is at week 6 during the course of therapy.

In particular embodiments, the method further comprises comparing the measured level of the one or more predictor variables to a reference level of the one or more predictor variables. In certain instances, a reference level of the one or more predictor variables can be established from IBD (e.g., UC) subjects on therapy with the drug who do not have detectable levels of autoantibodies (i.e., "not detectable"). In some embodiments, the method predicts that the subject will or will not develop autoantibodies to the anti-TNFα drug at a later time point during the course of therapy when the measured level of the predictor variable is less than, greater than, or equal to the reference level of the predictor variable.

As a non-limiting example, a subject is predicted to develop autoantibodies to infliximab (ATI) at week 6 if the level of IL-8 at week 2 is greater than a reference level of IL-8 (e.g., the level of IL-8 in a "not detectable" sample at week 2). As another non-limiting example, a subject is predicted to develop autoantibodies to infliximab (ATI) at week 6 if the level of anti-TNFα drug (e.g., IFX) at 24 hours after dosing is lower than a reference level of the anti-TNFα drug (e.g., the level of the anti-TNFα drug in a "not detectable" sample at 24 hours after dosing). As yet another non-limiting example, a subject is predicted to develop autoantibodies to infliximab (ATI) at week 6 if the TNFα/drug ratio at 24 hours after dosing is higher than a reference TNFα/drug ratio (e.g., the TNFα/drug ratio in a "not detectable" sample at 24 hours after dosing).

In other embodiments, the method further comprises applying a statistical analysis on the one or more predictor variables. In particular embodiments, the statistical analysis comprises a multiple logistic regression model. In certain embodiments, the statistical analysis predicts whether the subject will develop autoantibodies to the anti-TNFα drug at a later time point during the course of therapy.

As such, the methods and systems of the present invention advantageously enable a clinician to practice "personalized medicine" by guiding patient selection and prediction with respect to treatment decisions and informing therapy selection and optimization such that the right anti-TNFα drug is given to the right patient at the right time.

IV. Measuring TNFα, Anti-TNFα Drug, and Anti-Drug Antibody (ADA) Levels

In some embodiments, the presence and/or level of TNFα is detected, determined, or measured with a CEER™ (Collaborative Enzyme Enhanced Reactive) immunoassay. In CEER™ assays, an antibody-microarray based platform is utilized to form a unique "triple-antibody-enzyme-channeling" immuno-complex capable of measuring analytes of limited availability in a sample. For instance, a CEER™ assay using an anti-TNFα drug (e.g., infliximab (IFX), etanercept, adalimumab (ADL), certolizumab pegol, or golimumab) as a capture antibody can detect TNFα in serum at levels in the pg/mL range (e.g., about 0.1 pg/mL or more). The assay can have a sensitivity of less than about 0.2 pg/mL. The assays described can determine an analyte to less than 50 pg/mL, less than 25 pg/mL, less than 20 pg/mL, less than 10 pg/mL, less than 5 pg/mL, less 1 pg/mL or even less. A detailed description of CEER™ is found in, e.g., U.S. Pat. No. 8,163,499, which is hereby incorporated by reference in its entity for all purposes. CEER™ is also described in the following patent documents which are herein incorporated by reference in their entirety for all purposes: International Patent Publication Nos. WO 2008/036802, WO 2009/012140, WO 2009/108637, WO 2010/132723, WO 2011/008990, WO 2011/050069; WO 2012/088337; WO 2012/119113; and WO 2013/033623.

In other embodiments, an immunoassay such as a sandwich assay or ELISA can be used to measure TNFα. Non-limiting examples include Human TNF-α High Sensitivity ELISA (Cat. No. BMS223HS, eBioscience, San Diego, Calif.), Erenna Human TNFα immunoassay (Cat. No. 03-0022-xx, Singulex, Alameda, Calif.), Human TNFα cytokine assay (Cat. No. K151BHA-5, Meso Scale Diagnostics (MSD), Rockville, Md.)) and a muli-marker immunoassay (e.g., as described in U.S. Pat. No. 8,450,069; Singulex). The assays described can determine an analyte to less than 50 pg/mL, less than 25 pg/mL, less than 20 pg/mL, less than 10 pg/mL, less than 5 pg/mL, less 1 pg/mL or even less.

In some embodiments, the presence and/or level of an anti-TNFα drug and/or ADA (e.g., ATI formation) is detected, determined, or measured with a homogeneous mobility shift assay (HMSA) using size exclusion chromatography. These methods are described in U.S. Pat. No. 8,574,855; U.S. Patent Publication Nos. 2012/0329172 and 2014/0051184; and PCT Publication. No. WO2012/154987, the disclosures of which are hereby incorporated by reference in their entirety for all purposes. The methods are particularly useful for measuring the presence or level of TNFα inhibitors as well as autoantibodies (e.g., HACA, HAHA, etc.) that are generated against them.

V. Statistical Analysis

In certain aspects, the present invention provides models to predict the level of an anti-TNFα drug, the clinical outcome on anti-TNFα drug therapy, and/or the likelihood of developing anti-drug antibodies. In particular embodiments, the model is an algorithmic model which uses one or more predictor variables including TNFα level, anti-TNFα drug level, C-reactive protein (CRP) level, human serum albumin (HSA) level, immunomodulator (IMM) use, gender, age, age at diagnosis, Body Mass Index (BMI) at first drug dose, hemoglobin (Hb) level at first drug dose, age at first drug dose (years), surgery previous to first drug dose, ratio of TNFα level to drug level, presence of autoantibodies to the drug, IL12p40 level, IL-8 level, and combinations thereof.

An algorithmic model includes any of a variety of statistical methods and models used to determine relationships between variables. In the present invention, the variables are the values of the one or more predictor variables at an earlier time point during the course of anti-TNFα drug therapy (e.g., at week 2, 6, and/or 14) and/or prior to the initiation of the course of therapy (i.e., baseline or week 0). Any number of predictor variables can be analyzed using a statistical analysis described herein. For example, the value of 1, 2, 3, 4, 5, 6, 7, 8, 9, 10, 11, 12, 13, 14, 15, 16, 17, 18, 19, 20, 25, 30, 35, 40, 45, 50, 55, 60, or more predictor variables can be included in a statistical analysis such as, e.g., a multiple logistic regression model.

In particular embodiments, quantile analysis is applied to the value of one or more predictor variables to guide treatment decisions for patients receiving anti-TNFα drug therapy. In other embodiments, one or a combination of two or more statistical algorithms such as learning statistical classifier systems are applied to the value of one or more predictor variables to guide treatment decisions for patients receiving anti-TNFα drug therapy. The statistical analyses of the methods of the present invention advantageously assist in determining the initial dose an anti-TNFα drug, when or how to adjust or modify (e.g., increase or decrease) the subsequent dose of an anti-TNFα drug, to combine an anti-TNFα drug (e.g., at an increased, decreased, or same dose) with one or more immunosuppressive agents such as methotrexate (MTX) or azathioprine (AZA), and/or to change the current course of therapy (e.g., switch to a different anti-TNF drug).

The algorithmic model includes the value of one or more predictor variables along with a statistical algorithm such as a multiple logistic regression analysis. In certain instances, the model has been trained with known outcomes using a training set cohort of samples. The algorithm is then validated using a validation cohort. Patient unknown samples can then be predicted based on the trained algorithms.

The term "statistical analysis" or "statistical algorithm" or "statistical process" includes any of a variety of statistical methods and models used to determine relationships between variables. In the present invention, the variables are the values or measurements of the one or more predictor variables described herein. Any number of predictor variables can be analyzed using a statistical analysis described herein. In preferred embodiments, logistic regression is used (e.g., a multiple logistic regression model). In other embodiments, linear regression is used. In further embodiments, a Cox proportional hazards regression model is used.

In certain embodiments, the statistical analysis of the present invention comprises a quantile measurement of one or more predictor variables (e.g., markers such as anti-TNFα drug levels) within a given population. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In particular embodiments, the statistical analysis comprises one or more learning statistical classifier systems. As used herein, the term "learning statistical classifier system" includes a machine learning algorithmic technique capable of adapting to complex data sets (e.g., panel of predictor variables) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological samples) from healthy individuals, patients with the disease or disorder of interest (e.g., IBD patients such as CD and/or UC patients), and/or patients on therapy (e.g., anti-TNFα drug therapy). For example, samples from patients diagnosed by a physician, and preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

The statistical methods and models described herein can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The statistical methods and models described herein can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The statistical methods and models described herein can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The statistical methods and models described herein can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The statistical methods and models described herein can be selected for a disease prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

The statistical methods and models described herein can be selected such that the overall accuracy is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain embodiments, the statistical analysis comprises calculating or applying a hazard ratio (HR). In certain instances, the HR is calculated using a Cox Proportional Hazard Model. The Cox regression model provides an estimate of the hazard ratio and its confidence interval. The confidence interval provides an estimate of the precision of the HR. A large confidence interval indicates a lower HR precision, while a small confidence interval indicates an HR with a high precision. A p-value indicates whether the HR is statistically significant. In some embodiments, the hazard is the formation of anti-drug antibodies and the HR is the multiplicative effect on the hazard.

VI. Predictive Models and Systems

In some aspects, the present invention provides a system for predicting the level of an anti-TNFα drug in a subject at a later time point during a course of therapy with the anti-TNFα drug. In other aspects, the present invention provides a system for predicting whether a subject will develop autoantibodies to an anti-TNFα drug at a later time point during a course of therapy with the anti-TNFα drug. In yet other aspects, the present invention provides a system for predicting a clinical outcome of a subject at a later time point during a course of therapy with the anti-TNFα drug.

In certain embodiments, the system comprises: a data acquisition module configured to produce a data set comprising one or more predictor variables for the subject determined at an earlier time point during the course of therapy and/or prior to the initiation of the course of therapy; a data processing module configured to process the data set by applying a statistical analysis to the data set to produce a statistically derived decision predicting the level of the anti-TNFα drug or predicting whether the subject will develop autoantibodies to the anti-TNFα drug or predicting a clinical outcome of the subject receiving the anti-TNFα drug based upon the one or more predictor variables; and a display module configured to display the statistically derived decision.

In some embodiments, the system includes an intelligence module, such as a computer, having a processor and memory module. The intelligence module may also include communication modules for transmitting and receiving information over one or more direct connections (e.g., USB, Firewire, or other interface) and one or more network connections (e.g., including a modem or other network interface device). The memory module may include internal memory devices and one or more external memory devices. The intelligence module also includes a display module, such as a monitor, screen, or printer. In one aspect, the intelligence module receives data such as patient test results from a data acquisition module such as a test system, either through a direct connection or over a network. For example, the test system may be configured to run multianalyte tests on one or more patient samples and automatically provide the test results to the intelligence module. The data may also be provided to the intelligence module via direct input by a user or it may be downloaded from a portable medium such as a compact disk (CD) or a digital versatile disk (DVD). The test system may be integrated with the intelligence module, directly coupled to the intelligence module, or it may be remotely coupled with the intelligence module over the network. The intelligence module may also communicate data to and from one or more client systems over the network as is well known. For example, a requesting physician or healthcare provider may obtain and view a report from the intelligence module, which may be resident in a laboratory or hospital, using a client system.

The network can be a LAN (local area network), WAN (wide area network), wireless network, point-to-point network, star network, token ring network, hub network, or other configuration. As the most common type of network in current use is a TCP/IP (Transfer Control Protocol and Internet Protocol) network such as the global internetwork of networks often referred to as the "Internet" with a capital "I," that will be used in many of the examples herein, but it should be understood that the networks that the present invention might use are not so limited, although TCP/IP is the currently preferred protocol.

Several elements in the system may include conventional, well-known elements that need not be explained in detail here. For example, the intelligence module could be implemented as a desktop personal computer, workstation, mainframe, laptop, etc. Each client system could include a desktop personal computer, workstation, laptop, cell phone, tablet, PDA, or any WAP-enabled device or any other computing device capable of interfacing directly or indirectly to the Internet or other network connection. A client system typically runs an HTTP client, e.g., a browsing program, such as Microsoft's Internet Explorer™ browser, Google's Chrome browser, or a WAP-enabled browser or mobile application in the case of a cell phone, tablet, PDA, or other wireless device, or the like, allowing a user of the client system to access, process, and view information and pages available to it from the intelligence module over the network. Each client system also typically includes one or more user interface devices, such as a keyboard, a mouse, touch screen, pen, or the like, for interacting with a graphical user interface (GUI) provided by the browser on a display (e.g., monitor screen, cell phone or tablet screen, LCD display, etc.) in conjunction with pages, forms, and other information provided by the intelligence module. As discussed above, the present invention is suitable for use with the Internet, which refers to a specific global internetwork of networks. However, it should be understood that other networks can be used instead of the Internet, such as an intranet, an extranet, a virtual private network (VPN), a non-TCP/IP based network, any LAN or WAN, or the like.

According to one embodiment, each client system and all of its components are operator configurable using applications, such as a browser, including computer code run using a central processing unit such as an Intel® Pentium® processor or the like. Similarly, the intelligence module and all of its components might be operator configurable using application(s) including computer code run using a central processing unit such as an Intel® Pentium® processor or the like, or multiple processor units. Computer code for operating and configuring the intelligence module to process data and test results as described herein is preferably downloaded and stored on a hard disk, but the entire program code, or portions thereof, may also be stored in any other volatile or non-volatile memory medium or device as is well known, such as a ROM or RAM, or provided on any other computer readable medium capable of storing program code, such as a compact disk (CD) medium, digital versatile disk (DVD) medium, a floppy disk, ROM, RAM, and the like.

The computer code for implementing various aspects and embodiments of the present invention can be implemented in any programming language that can be executed on a computer system such as, for example, in C, C++, C #, HTML, Java, JavaScript, or any other scripting language, such as VBScript. Additionally, the entire program code, or portions thereof, may be embodied as a carrier signal, which may be transmitted and downloaded from a software source (e.g., server) over the Internet, or over any other conventional network connection as is well known (e.g., extranet, VPN, LAN, etc.) using any communication medium and protocols (e.g., TCP/IP, HTTP, HTTPS, Ethernet, etc.) as are well known.

VII. Examples

The present invention will be described in greater detail by way of specific examples. The following examples are offered for illustrative purposes, and are not intended to limit the present invention in any manner. Those of skill in the art will readily recognize a variety of noncritical parameters which can be changed or modified to yield essentially the same results.

Example 1. Prediction of the Formation of Antibodies-to-Infliximab (ATI) Based on Infliximab (IFX) Levels This example illustrates the association between infliximab (IFX) levels and the formation of antibodies-to-IFX (ATI) in Crohn's disease (CD) patients at various time points during the course of IFX therapy. In certain aspects, this example shows that the level of an anti-TNFα drug (e.g., IFX) at an earlier time point during therapy is predictive of anti-TNFα drug autoantibody (e.g., ATI) formation at a later time point during therapy. In other aspects, this example shows that anti-TNFα drug (e.g., IFX) levels above a specific threshold or cut-off value (i.e., drug levels in the $4^{th}$ quartile or Q4 based on quartile analysis) at an earlier time point during therapy is predictive of whether a patient will develop anti-TNFα drug autoantibody (e.g., ATI) at a later time point during therapy.

Figure 1B:
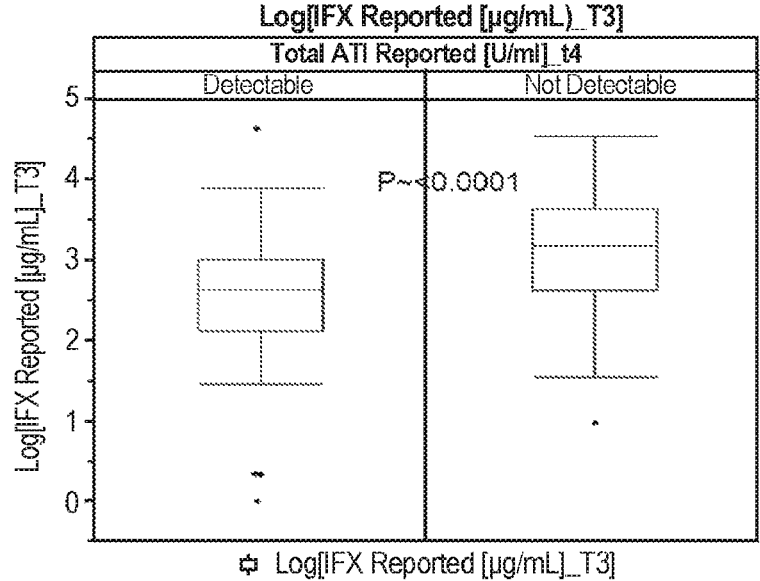
Figure 1C:
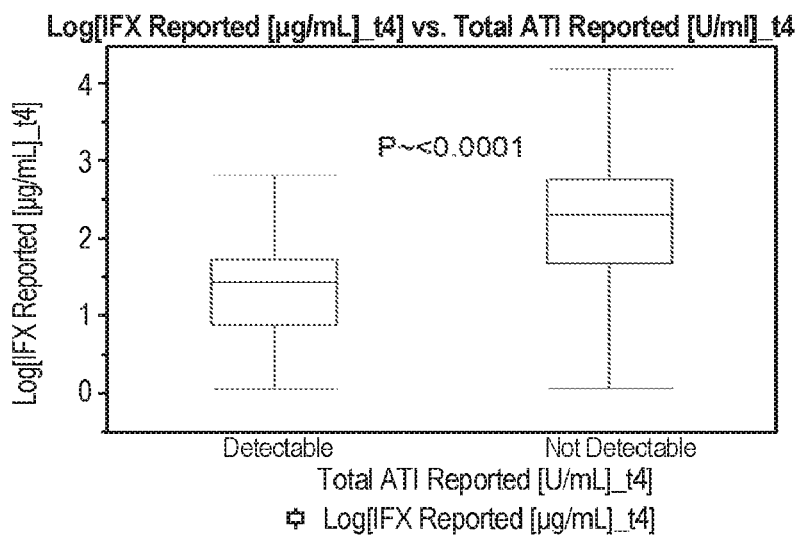

FIGS. 1A-1C show the relationship between IFX levels and the ATI formation in CD patients at week 2 ("t2"), week 6 ("t3"), and week 14 ("t4") following the initiation of IFX therapy (baseline or week 0 or "t1"). In particular, FIGS. 1A-1C illustrate that IFX levels at week 2 (FIG. 1A), week 6 (FIG. 1B), and week 14 (FIG. 1C) can be used to predict whether or not ATI would be detected at week 14. As such, FIGS. 1A-1C demonstrate that the level of an anti-TNFα drug (e.g., IFX) at an earlier time point during therapy (e.g., at week 6) is predictive of anti-TNFα drug autoantibody (e.g., ATI) formation at a later time point during therapy (e.g., at week 14).

FIG. 2 shows the association between TNFα, IFX, C-reactive protein (CRP), and human serum albumin (HSA) with ATI formation (p-values) at baseline (week 0), and at weeks 2, 6, and 14 following IFX therapy. In particular, FIG. 2 illustrates that only IFX levels were predictive of ATI formation after 14 weeks of therapy.

FIG. 3 shows a stratified analysis of the association between IFX levels and ATI formation in CD patients receiving IFX monotherapy or combination therapy with IFX and an immunosuppressive agent (e.g., immunomodulator or "IMM") such as azathioprine (AZA), 6-mercaptopurine (6-MP), or methotrexate (MTX). In particular, FIG. 3 illustrates that IFX levels at weeks 2 and 6 predict ATI formation at week 14 only in patients receiving monotherapy.

Figure 4:
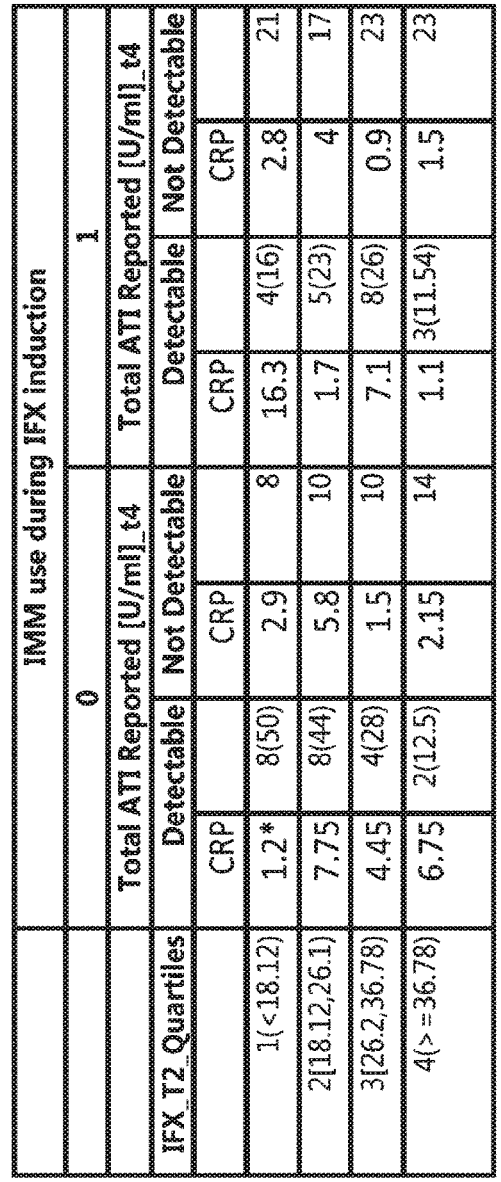
FIG. 4 shows the results of a quartile analysis that was performed to further characterize the association between IFX levels at week 2 and ATI formation at week 14.
Figure 17:
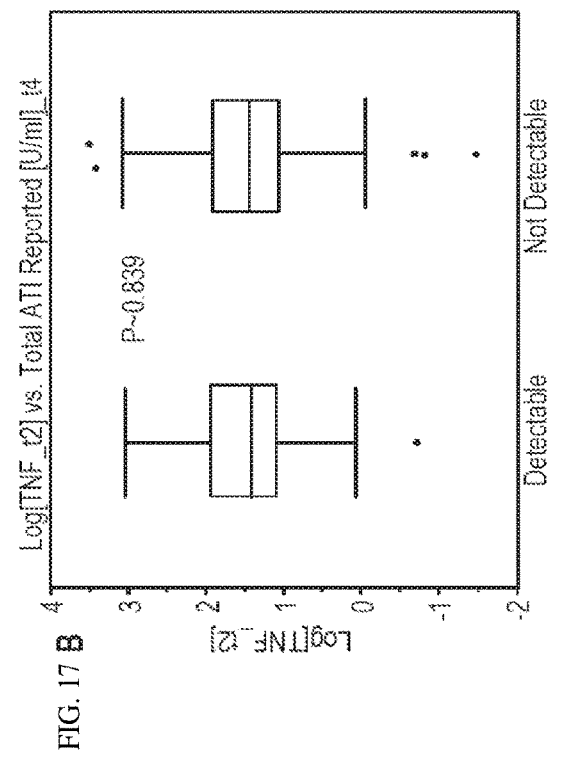
FIGS. 17A-17D show the relationship between TNFα levels at baseline (FIG. 17A), week 2 (FIG. 17B), week 6 (FIG. 17C), and week 14 (FIG. 17D) and ATI formation at week 14.
Figure 17:
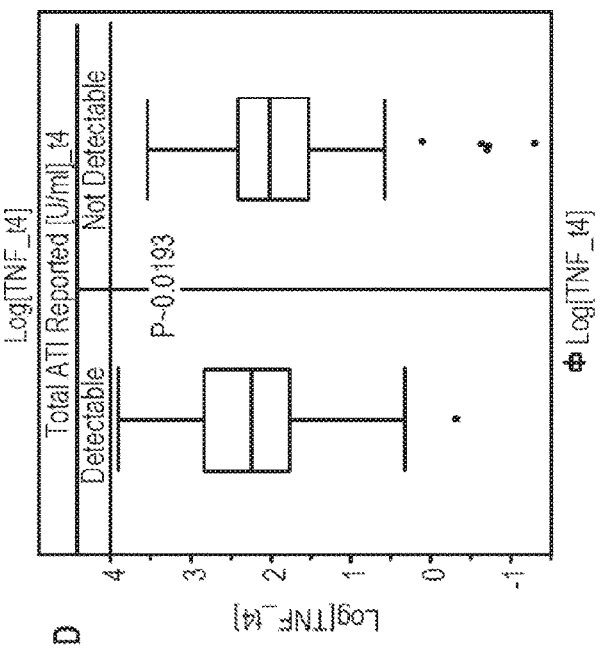
Figure 17:
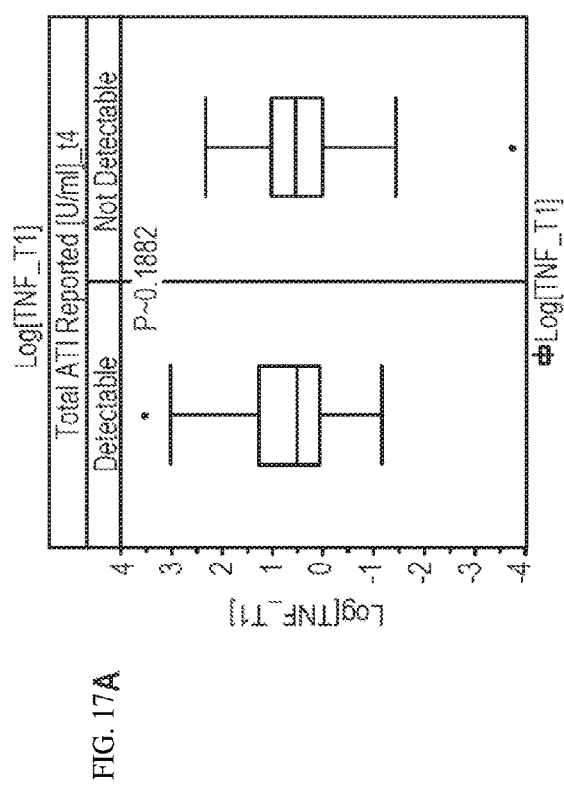
Figure 17:
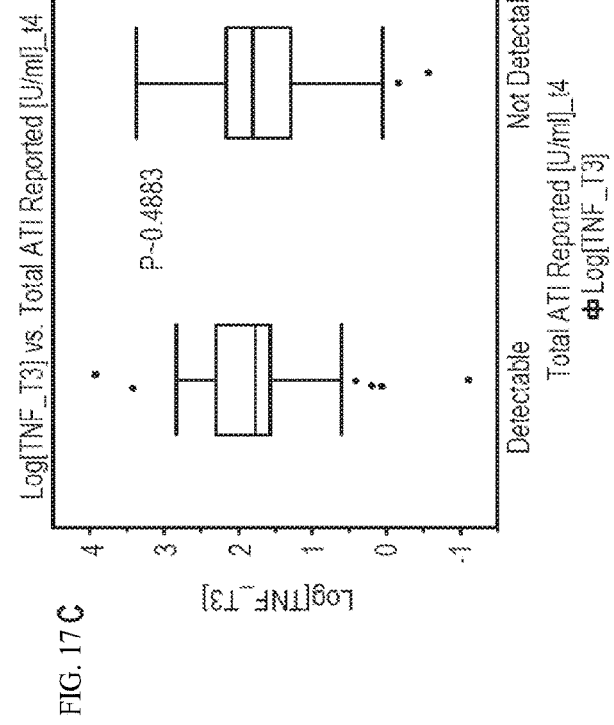

FIG. 4 shows the results of a quartile analysis that was performed to further characterize the association between IFX levels at week 2 and ATI formation at week 14. In particular, FIG. 4 illustrates that IFX drug levels at week 2 should be greater than 37 μg/ml (i.e., $4^{th}$ quartile or Q4) to prevent ATI formation at week 14, independent of whether the patient is receiving IFX monotherapy or combination therapy.

FIG. 5 shows the results of a quartile analysis that was performed to further characterize the association between IFX levels at week 6 and ATI formation at week 14. In particular, FIG. 5 illustrates that IFX drug levels at week 6 should be greater than 35 µg/ml (i.e., $4^{th}$ quartile or Q4) to prevent ATI formation at week 14, independent of whether the patient is receiving IFX monotherapy or combination therapy.

FIG. 6 shows the results of a quartile analysis that was performed to further characterize the association between IFX levels at week 14 and ATI formation at week 14. CRP level at week 14 is presented as its median. In particular, FIG. 6 illustrates that IFX drug levels at week 14 should be greater than 14 µg/ml (i.e., $4^{th}$ quartile or Q4) to prevent ATI formation at week 14, independent of whether the patient is receiving IFX monotherpy or combination therapy.

Example 2. Multiple Regression Models for Predicting IFX Levels and ATI Formation This example illustrates multiple regression modelling to predict IFX levels and ATI formation at a later time point during a course of therapy with IFX (e.g., at week 2, 6, or 14) in Crohn's disease (CD) patients prior to the initiation of IFX therapy. In certain aspects, this example shows that the initial dose of an anti-TNFα drug (e.g., IFX) can be individualized and tailored for each patient at the start of therapy based on the predictive models described herein. In other aspects, this example shows that patients predicted to produce anti-TNFα drug autoantibody (e.g., ATI) during a course of therapy with an anti-TNFα drug (e.g., IFX) based on the predictive models described herein can be administered an initial dose of the drug that is increased compared to the normal starting dose and/or an increased dose of an immunosuppressive agent (e.g., immunomodulator or "IMM") such as azathioprinc (AZA), 6-mercaptopurine (6-MP), or methotrexate (MTX).

Table 1 shows non-limiting examples of variables that were used in the multiple regression models described herein to predict IFX levels at week 2 ("12"), week 6 ("t3"), and week 14 ("t4") following the initiation of IFX therapy (baseline or week 0 or "t1") and to predict ATI formation at week 14 following the initiation of IFX therapy.

TABLE 1

| variables | Monotherapy | | | | Combination therapy | | | | p-value |
| --- | --- | --- | --- | --- | --- | --- | --- | --- | --- |
| | Mean | Std Dev | Median | N | Mean | Std Dev | Median | N | |
| age | 43.78 | 15.22 | 41.00 | 74 | 38.43 | 14.12 | 35.00 | 127 | 0.0148 |
| Gender (Female freq) | 0.60 | | | 44 | 0.52 | | | 66 | 0.3782 |
| Age at diagnosis | 29.24 | 12.67 | 26.00 | 74 | 26.72 | 11.62 | 23.00 | 127 | 0.1635 |
| BMI at 1st IFX | 23.15 | 4.33 | 23.00 | 74 | 23.04 | 4.01 | 23.00 | 121 | 0.86 |
| Age at 1st IFX (years) | 39.92 | 15.00 | 38.00 | 74 | 35.07 | 14.15 | 32.00 | 127 | 0.0255 |
| TNF_T1 | 2.18 | 2.57 | 1.54 | 74 | 2.16 | 1.75 | 1.71 | 126 | 0.25 |
| TNF_t2 | 6.10 | 5.58 | 4.72 | 71 | 5.16 | 3.77 | 4.16 | 122 | 0.66 |
| TNF_T3 | 8.04 | 7.99 | 5.78 | 74 | 6.83 | 4.34 | 5.93 | 124 | 0.92 |
| TNF_t4 | 10.43 | 8.81 | 8.47 | 67 | 8.34 | 6.23 | 7.50 | 106 | 0.16 |
| IFX Reported [µg/mL]_t2 | 25.97 | 12.30 | 24.12 | 71 | 27.24 | 12.40 | 28.64 | 122 | 0.67 |
| IFX Reported [µg/mL]_T3 | 21.82 | 14.93 | 16.80 | 74 | 25.11 | 15.45 | 22.75 | 124 | 0.0471 |
| IFX Reported [µg/mL]_t4 | 9.09 | 9.65 | 6.64 | 67 | 10.46 | 9.96 | 8.85 | 107 | 0.24 |
| CRP_w0 (mg/L) | 22.11 | 32.27 | 10.65 | 74 | 18.87 | 25.28 | 9.90 | 127 | 0.74 |
| CRP_w2 | 4.93 | 6.50 | 2.25 | 74 | 5.99 | 13.08 | 1.60 | 125 | 0.67 |
| CRP_w6 | 5.29 | 8.18 | 2.00 | 73 | 4.32 | 6.80 | 1.50 | 127 | 0.34 |
| CRP_w14 | 5.76 | 9.16 | 2.20 | 67 | 5.51 | 9.41 | 1.60 | 110 | 0.74 |
| Albumin_w0 (g/dL) | 4.05 | 0.46 | 4.07 | 74 | 4.16 | 0.38 | 4.16 | 127 | 0.074 |
| Albumin_w2 | 4.20 | 0.44 | 4.25 | 73 | 4.26 | 0.36 | 4.25 | 124 | 0.27 |
| Albumin_w6 | 4.27 | 0.41 | 4.35 | 70 | 4.35 | 0.38 | 4.37 | 126 | 0.19 |
| Albumin_w14 | 4.30 | 0.34 | 4.31 | 65 | 4.40 | 0.39 | 4.40 | 107 | 0. |

FIG. 7 shows the results of multiple regression modelling to predict IFX levels at week 14 using baseline (week 0 or "t1") measures of the following initial predictor variables: TNFα at t1 (TNF_T1); CRP at t1 (CRP_w0 (mg/L)); albumin at t1 (Albumin_w0 (g/dL)); immunomodulator (IMM); gender; age; age at diagnosis; Body Mass Index (BMI) at 1st IFX; hemoglobin at 1st IFX; age at 1st IFX (years); and previous surgery (i.e., surgery previous to 1st IFX). In particular, FIG. 7 illustrates that the best model used baseline values of TNFα (i.e., Log[TNF_T1]), albumin, age, and BMI to predict drug levels at week 14 with about 16% accuracy (see. "RSquare Adj").

FIG. 8 shows the results of multiple regression modelling to predict IFX levels at week 2 using baseline (week 0 or "t1") measures of the following initial predictor variables: TNFα at t1 (TNF_T1); CRP at t1 (CRP_0 (mg/L)); albumin at t1 (Albumin_w0 (g/dL)); immunomodulator (IMM); gender; age; age at diagnosis; Body Mass Index (BMI) at 1st IFX; hemoglobin at 1st IFX; age at 1st IFX (years); and previous surgery. In particular, FIG. 8 illustrates that the best model used baseline values of CRP (i.e., Log[CRP_w0 (mg/L)]), albumin, gender, and BMI to predict drug levels at week 2 with about 27% accuracy (see. "RSquare Adj").

FIG. 9 shows the results of multiple regression modelling to predict IFX levels at week 6 using baseline (week 0 or "t") and week 2 ("t2") measures of the following initial predictor variables: TNFα at t1 (TNF_T1): CRP at t1 (CRP_w0 (mg/L)); albumin at t1 (Albumin_w0 (g/dL)): imnmunomodulator (IMM) use during IFX induction; gender; age; age at diagnosis; Body Mass Index (BMI) at 1st IFX; hemoglobin at 1st IFX; age at 1st IFX (years): previous surgery; IFX at t2 (IFX Reported [µg/mL]_t2): ATI at t2 (Total ATI Reported [U/ml]_T2): TNFα at t2 (TNF_t2);

CRP at t2 (CRP_w2): and albumin at t2 (Albumin_w2). In particular, FIG. 9 illustrates that the best model used baseline values of IMM use during IFX induction and previous surgery, and week 2 values of IFX (i.e., Log[IFX Reported [µg/mL]_t2]) and CRP (i.e., Log[CRP_w2]) to predict drug levels at week 6 with about 40% accuracy (see, "RSquare Adj").

FIG. 10 shows the results of multiple regression modelling to predict IFX levels at week 14 using baseline (week 0 or "t1"), week 2 ("t2"), and week 6 ("t3") measures of the following initial predictor variables: TNFα at t1 (TNF_T1); CRP at t1 (CRP_w0 (mg/L)); albumin at t1 (Albumin_w0 (g/dL)); immunomodulator (IMM) use during IFX induction; gender; age; age at diagnosis; Body Mass Index (BMI) at 1st IFX; hemoglobin at 1st IFX; age at 1st IFX (years); previous surgery; IFX at t2 (IFX Reported [µg/mL]_t2); ATI at t2 (Total ATI Reported [U/ml]_T2); TNFα at t2 (TNF_t2); CRP at t2 (CRP_w2); albumin at t2 (Albumin_w2); IFX at t3 (IFX Reported [µg/mL]_T3); ATI at t3 (Total ATI Reported [U/ml]_T3); TNFα at t3 (TNF_T3); CRP at t3 (CRP_w6); and albumin at t3 (Albumin_w6). In particular, FIG. 10 illustrates that the best model used baseline values of age at 1st IFX (years), week 2 values of IFX (i.e., Log[IFX Reported [µg/mL]_t2]), and week 6 values of IFX (i.e., Log[IFX Reported [µg/mL]_T3]), total ATI, and CRP (i.e., Log[CRP_w6]) to predict drug levels at week 14 with about 51.1% accuracy (see, "RSquare Adj").

FIG. 11 shows the results of multiple regression modelling to predict IFX levels at week 14 using baseline (week 0 or "t1"), week 2 ("t2"), and week 6 ("t3") measures of the same initial predictor variables described for FIG. 10, but enforcing TNFα in the model. In particular, FIG. 11 illustrates that the best model used baseline values of age at 1st IFX (years), week 2 values of IFX (i.e., Log[IFX Reported [µg/mL]_t2]), and week 6 values of IFX (i.e., Log[IFX Reported [µg/mL]_T3]), total ATI, TNFα (i.e., Log [TNF_T3]), and CRP (i.e., Log[CRP_w6]) to predict drug levels at week 14 with about 51.2% accuracy (see, "RSquare Adj").

FIG. 12 shows the results of multiple logistic regression modelling to predict ATI formation at week 14 using baseline (week 0 or "t1") measures of the following initial predictor variables: TNFα at t1 (TNF_T1); CRP at t1 (CRP_w0 (mg/L)); albumin at t1 (Albumin_w0 (g/dL)); immunomodulator (IMM); gender; age; age at diagnosis; Body Mass Index (BMI) at 1st IFX; hemoglobin at 1st IFX; age at 1st IFX (years); and previous surgery. In particular, FIG. 12 illustrates that the best model used baseline values of TNFα (i.e., Log[TNF_T1]), gender, hemoglobin at 1st IFX, and IMM use during IFX induction to predict ATI formation at week 14 with about 72% accuracy (see, AUC value).

FIG. 13 shows the results of multiple logistic regression modelling to predict ATI formation at week 14 using baseline (week 0 or "t1") and week 2 ("t2") measures of the following initial predictor variables: TNFα at t1 (TNF_T1); CRP at t1 (CRP_w0 (mg/L)); albumin at t1 (Albumin_w0 (g/dL)); immunomodulator (IMM) use during IFX induction; gender; age; age at diagnosis; Body Mass Index (BMI) at 1st IFX; hemoglobin at 1st IFX; age at 1 st IFX (years); previous surgery; TNFα at t2 (TNF_t2); CRP at t2 (CRP_w2); albumin at t2 (Albumin_w2); and IFX at t2 (IFX Reported [µg/mL]_t2). In particular, FIG. 13 illustrates that the best model used baseline values of TNFα (i.e., Log [TNF_T1]), IMM use during IFX induction, gender, and hemoglobin at 1st IFX, and week 2 values of albumin and IFX (i.e., Log[IFX Reported [µg/mL]_t2]) to predict ATI formation at week 14 with about 76% accuracy (see, AUC value).

FIG. 14 shows the results of multiple logistic regression modelling to predict ATI formation at week 14 using baseline (week 0 or "t1"), week 2 ("t2"), and week 6 ("t3") measures of the following initial predictor variables: TNFα at t1 (TNF_T1); CRP at t1 (CRP_w0 (mg/L)); albumin at t1 (Albumin_w0 (g/dL)); immunomodulator (IMM) use during IFX induction; gender; age; age at diagnosis; Body Mass Index (BMI) at 1st IFX; hemoglobin (Hb) at 1st IFX; age at 1st IFX (years); previous surgery; IFX at t2 (IFX Reported [µg/mL]_t2); ATI at t2 (Total ATI Reported [U/ml]_T2); TNFα at t2 (TNFα 2); CRP at t2 (CRP_w2); albumin at t2 (Albumin_w2); IFX at t3 (IFX Reported [µg/mL]_T3); ATI at t3 (Total ATI Reported [U/ml]_T3); TNFα at t3 (TNF_T3); CRP at t3 (CRP_w6); and albumin at t3 (Albumin_w6). In particular, FIG. 14 illustrates that the best model used baseline values of TNFα (i.e., Log[TNF_T1]), gender, and hemoglobin at 1st IFX, and week 6 values of albumin and IFX (i.e., Log[IFX Reported [µg/mL]_T3]) to predict ATI formation at week 14 with about 78% accuracy (see, AUC value).

FIG. 15 shows the results of multiple logistic regression modelling to predict ATI formation at week 14 using all time point measurements (i.e., baseline (week 0 or "t1"), week 2 ("t2"), week 6 ("t3"), and week 14 ("t4")) of the following initial predictor variables: TNFα at t1 (TNF_T1); CRP at t1 (CRP_w0 (mg/L)); albumin at t1 (Albumin_w0 (g/dL)); immunomodulator (IMM) use during IFX induction; gender; age; age at diagnosis; Body Mass Index (BMI) at 1st IFX; hemoglobin (Hb) at 1st IFX; age at 1st IFX (years); previous surgery; IFX at t2 (IFX Reported [µg/mL]_t2); ATI at t2 (Total ATI Reported [U/ml]_T2); TNFα at t2 (TNF_t2); CRP at t2 (CRP_w2); albumin at t2 (Albumin_w2); IFX at t3 (IFX Reported [µg/mL]_T3); ATI at t3 (Total ATI Reported [U/ml]_T3); TNFα at t3 (TNF_T3); CRP at t3 (CRP_w6); albumin at t3 (Albumin_w6); TNFα at t4 (TNF_T4); IFX at t4 (IFX Reported [µg/mL]_t4); CRP at t4 (CRP_w14); and albumin at t4 (Albumin_w14). In particular, FIG. 15 illustrates that the best model used baseline values of CRP (i.e., Log[CRP_w0 (mg/L)]), gender, and hemoglobin at 1st IFX, week 2 values of TNFα (i.e., Log[TNF_t2]), week 6 values of albumin, and week 14 values of TNFα (i.e., Log[TNF_t4]), IFX (i.e., Log[IFX Reported [µg/mL]_t4]), and CRP (i.e., Log[CRP_w14]) to predict ATI formation at week 14 with about 95% accuracy (see, AUC value).

FIG. 16 shows the results of multiple logistic regression modelling to predict ATI formation at week 14 using all time point measurements (i.e., baseline (week 0 or "t1"), week 2 ("t2"), week 6 ("t3"), and week 14 ("t4")) of the following initial predictor variables: TNFα at t1 (TNF_T1); CRP at t1 (CRP_w0 (mg/L)); albumin at t1 (Albumin_w0 (g/dL)); immunomodulator (IMM) use during IFX induction; gender; age; age at diagnosis; Body Mass Index (BMI) at 1st IFX; hemoglobin (Hb) at 1st IFX; age at 1st IFX (years); previous surgery; TNFα/IFX ratio at t2 (TNF2/IFX Reported [µg/mL]_t2); ATI at t2 (Total ATI Reported [U/ml]_T2); TNFα at t2 (TNF_t2); CRP at t2 (CRP_w2); albumin at t2 (Albumin_w2); TNFα/IFX ratio at t3 (TNF3/ IFX Reported [µg/mL]_T3); ATI at t3 (Total ATI Reported [U/ml]_T3); CRP at t3 (CRP_w6); albumin at t3 (Albumin_w6); TNFα/IFX ratio at t4 (TNF4/IFX Reported [µg/ mL]_t4); CRP at t4 (CRP_w14); and albumin at t4 (Albumin_w14). In particular, FIG. 16 illustrates that the best model used baseline values of CRP (i.e., Log[CRP_w0

(mg/L)]), gender, and hemoglobin at 1st IFX, week 2 values of TNFα (i.e., Log[TNF_t2]), week 6 values of albumin, and week 14 values of TNFα/IFX ratio (i.e., Log[TNF4/IFX4]) and CRP (i.e., Log[CRP_w14]) to predict ATI formation at week 14 with about 94% accuracy (see, AUC value).

Example 3. Prediction of IFX Levels and ATI Formation Based on TNFα Levels

This example illustrates the association between TNFα levels and IFX levels, ATI formation, human serum albumin (HSA) levels, and C-reactive protein (CRP) levels during the course of IFX therapy and at baseline prior to the initiation of therapy.

FIGS. 17A-17D show the relationship between TNFα levels at baseline (FIG. 17A), week 2 (FIG. 17B), week 6 (FIG. 17C), and week 14 (FIG. 17D) and ATI formation at week 14.

FIG. 18 shows the association between TNFα levels at baseline and IFX levels at weeks 2, 6, and 14. In particular, FIG. 18 illustrates that TNFα levels at baseline predict IFX levels at week 14.

FIG. 19 shows a stratified analysis of the association between baseline TNFα levels and IFX levels in CD patients receiving IFX monotherapy or combination therapy with IFX and an immunosuppressive agent. In particular, FIG. 19 illustrates that TNFα levels at baseline predict IFX levels at week 14 in patients receiving monotherapy.

FIG. 20 shows the association between HSA levels and TNFα levels. In particular, FIG. 20 illustrates that there is an inverse relationship between HSA levels and TNFα levels at weeks 0, 2, and 6.

FIG. 21 shows the association between CRP levels and TNFα levels. In particular, FIG. 21 illustrates that there is an association between baseline CRP levels and baseline TNFα levels.

Example 4. Prediction of CRP Levels and ATI Formation Based on Ratios of TNFα to IFX Levels This example illustrates the association between TNFα/IFX ratios and C-reactive protein (CRP) levels and ATI formation during the course of IFX therapy and at baseline prior to the initiation of therapy.

FIG. 22 shows the association between TNFα/IFX ratios and CRP levels. In particular, FIG. 22 illustrates that ratios of TNFα/IFX at weeks 2, 6, and 14 predict CRP levels at week 14.

FIG. 23 shows a stratified analysis of the association between ratios of baseline TNFα levels to IFX levels at different time points and CRP levels at week 14 in CD patients receiving IFX monotherapy or combination therapy with IFX and an immunosuppressive agent. In particular, FIG. 23 illustrates that ratios of baseline TNFα levels to IFX levels at week 6 predict CRP levels at week 14 in patients receiving combination therapy.

FIG. 24 shows a stratified analysis of the association between ratios of TNFα levels to IFX levels at different time points and CRP levels at week 14 in CD patients receiving IFX monotherapy or combination therapy with IFX and an immunosuppressive agent. In particular, FIG. 24 illustrates that ratios of TNFα levels to IFX levels at week 14 predict CRP levels at week 14 in patients receiving combination therapy.

FIG. 25 shows a stratified analysis of the association between ratios of TNFα levels to IFX levels at different time points and ATI formation at week 14 in CD patients receiving IFX monotherapy or combination therapy with IFX and an immunosuppressive agent. In particular, FIG. 25 illustrates that ratios of TNFα levels to IFX levels at week 6 predict ATI formation at week 14 in patients receiving monotherapy and ratios of TNFα levels to IFX levels at week 14 predict ATI formation at week 14 in patients receiving monotherapy or combination therapy.

Example 5. Prediction of CRP Levels Based on IFX Levels

This example illustrates the association between IFX levels and CRP levels. In particular, FIG. 26 shows that there is an inverse relationship between IFX levels and CRP levels at weeks 0, 2, and 6 during the course of therapy. As such, IFX levels at weeks 2, 6, and 14 predict CRP levels at week 14.

Example 6. Prediction of IFX and CRP Levels Based on HSA Levels

This example illustrates the association between baseline human serum albumin (HSA) levels and IFX levels during the course of therapy. In particular, FIG. 27 shows that there is an association between baseline HSA levels and IFX levels at weeks 2, 6, and 14. As such, baseline HSA levels predict IFX levels during the course of therapy.

This example also illustrates the association between CRP levels and HSA levels at baseline and at different time points during the course of therapy. In particular, FIG. 28 shows that there is an inverse relationship between CRP levels and HSA levels at baseline and at weeks 2, 6, and 14. FIG. 28 also shows that HSA levels at baseline predict CRP levels at week 14.

Example 7. Biomarkers for Predicting Clinical Outcome and ATI Formation

This example illustrates that biomarkers such as IL12p40, IL-8, and IFX at certain time points during the course of IFX therapy are associated with clinical outcome. This example also illustrates that biomarkers such as IL-8 and IFX at certain time points during the course of IFX therapy are associated with ATI formation at a later time point.

The IFX dosing scheme for the ulcerative colitis (UC) patients enrolled in this study was as follows: Week 0=24 hours after dosing (T0); Week 2=before $2^{nd}$ infusion (T5); and Week 6=before $3^{rd}$ infusion (T9). Clinical outcome was defined as the endoscopic response at week 8. There were 8 non-responders and 11 responders in the patient cohort. The following biomarkers were assayed in patient samples: IFN-g, IL-B, IL-2, IL-4, IL-6, IL-8, IL-10, IL-12p70, IL-13, GMCSF, IL12p40, IFX, TNFα, and ATI. The following time points were considered for analysis: T0, T5, and T9. As described in this example, IL12p40 levels at T5, IL-8 levels at T5, and IFX levels at T0 ($1^{st}$ dose) were associated with clinical outcome, while IL-8 levels at T5 and IFX levels at T0 were associated with ATI formation at T9 (i.e., within the first 6 weeks of IFX therapy).

Figure 29:
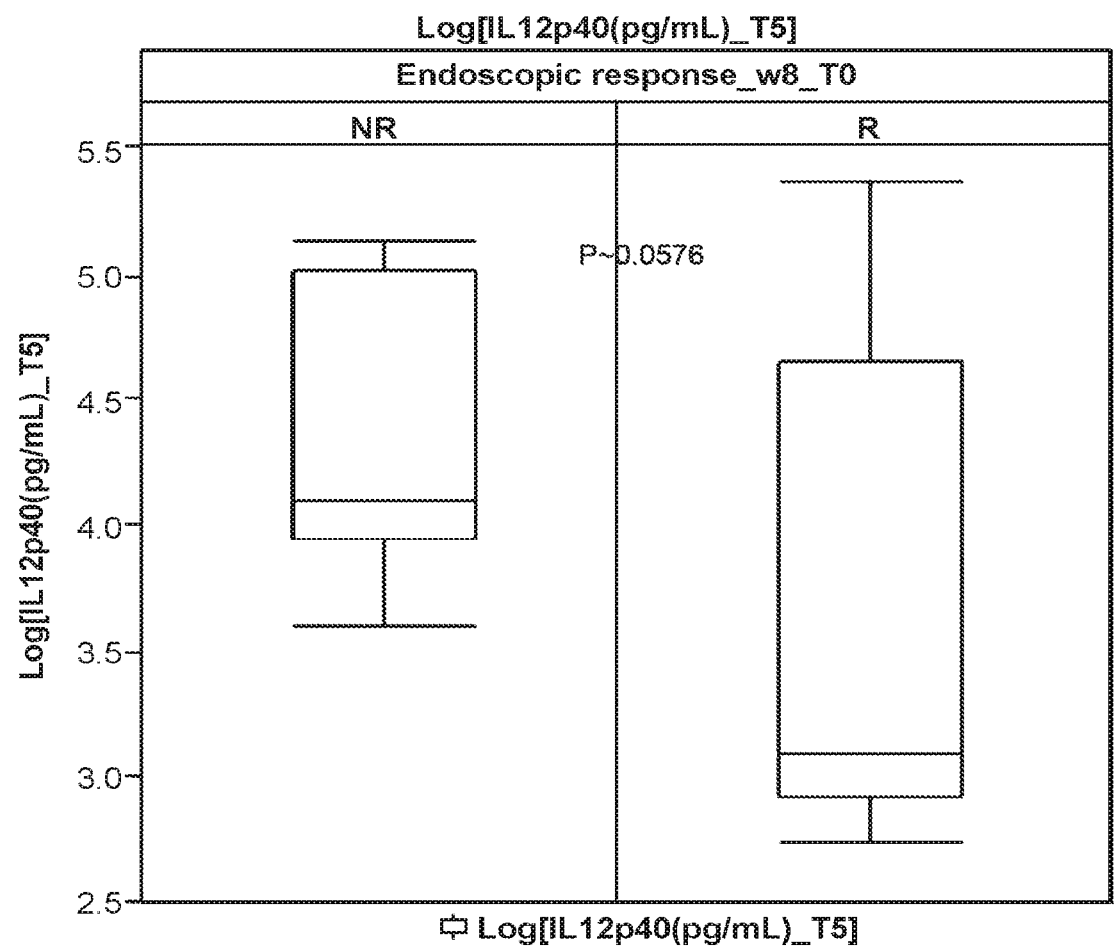
FIG. 29 shows the association between IL12p40 levels at T5 (week 2) and endoscopic response at week 8.

FIG. 29 shows the association between IL12p40 levels at T5 and endoscopic response at week 8. In particular, elevated levels of IL12p40 at T5 (week 2) were associated with non-response at week 8. These results illustrate that inflammation is also driven by IL12p40, not just TNFα. Patients with elevated IL12p40 levels should be administered combination therapy with an anti-IL12p40 drug such as Stelara® (ustekinumab) and an anti-TNFα drug. These results also illustrate that IL12p40 levels at week 2 can be used to predict clinical outcome (e.g., endoscopic response) at week 8. Similarly, the consistent trend observed in the data indicates that IL12p40 levels at T9 (week 6) can be used to predict clinical outcome (e.g., endoscopic response) at week 16.

Figure 30:
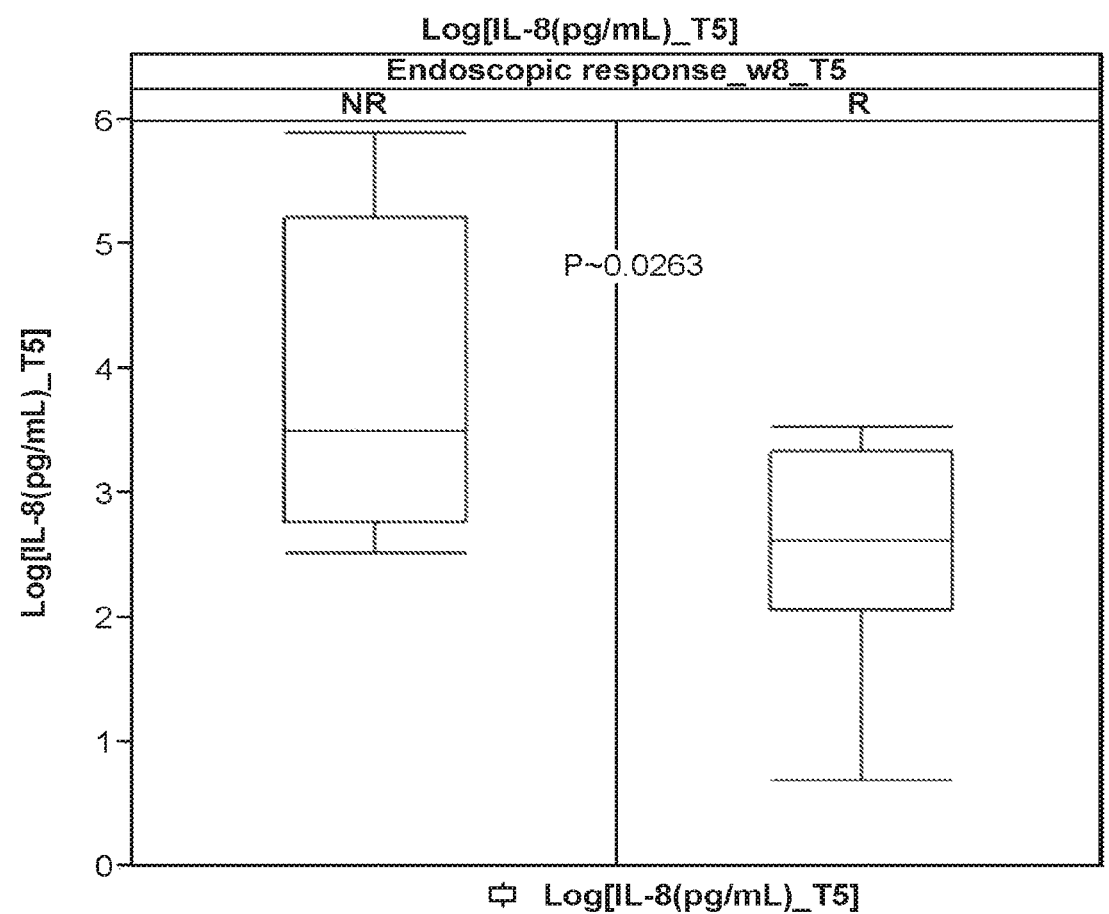
FIG. 30 shows the association between IL-8 levels at T5 (week 2) and endoscopic response at week 8.

FIG. 30 shows the association between IL-8 levels at T5 and endoscopic response at week 8. In particular, elevated levels of IL-8 at T5 (week 2) were associated with non-response at week 8. These results illustrate that IL-8 levels at week 2 can be used to predict clinical outcome (e.g., endoscopic response) at week 8. Similarly, the consistent trend observed in the data indicates that IL-8 levels at T9 (week 6) can be used to predict clinical outcome (e.g., endoscopic response) at week 16.

Figure 31:
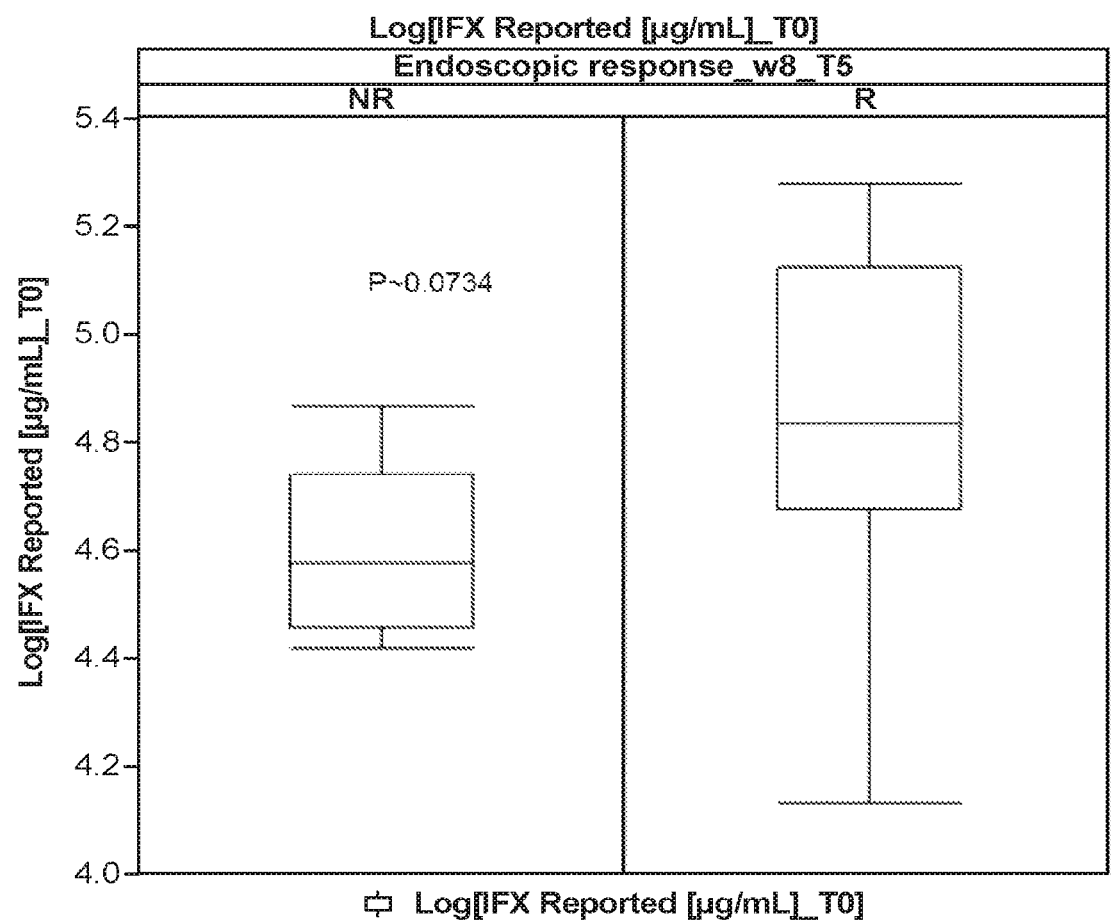
FIG. 31 shows the association between IFX drug levels at T0 (24 hours after dosing) and endoscopic response at week 8.

FIG. 31 shows the association between IFX drug levels at T0 and endoscopic response at week 8. In particular, low levels of IFX at T0 (24 hours after dosing) were associated with non-response at week 8. These results illustrate that IFX levels 24 hours after dosing can be used to predict clinical outcome (e.g., endoscopic response) at week 8.

Figure 32:
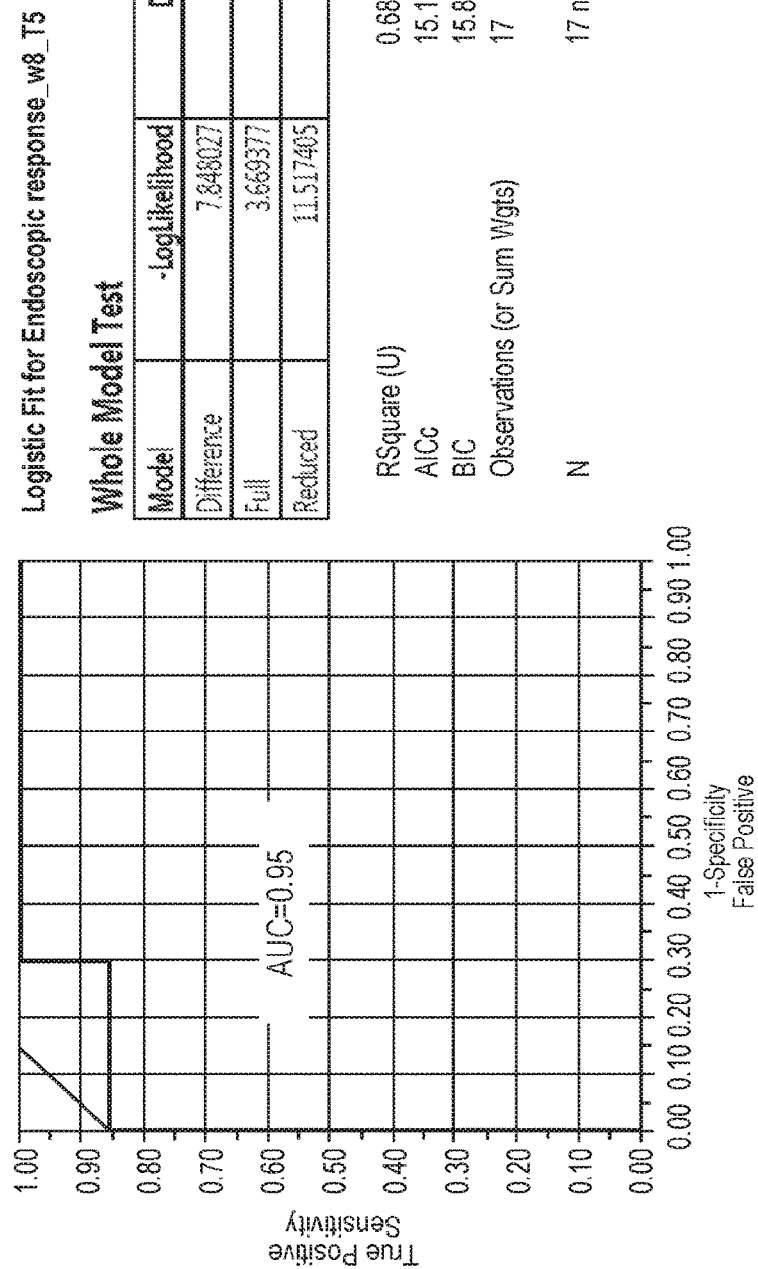
FIG. 32 shows the results of multiple regression modelling to predict clinical outcome (e.g., endoscopic response) at week 8.

FIG. 32 shows the results of multiple regression modelling to predict clinical outcome (e.g., endoscopic response) at week 8. In particular, FIG. 32 illustrates that using IL12p40 and IL-8 levels at T5 (week 2) as the predictor variables provided a prediction of endoscopic response at week 8 with an area-under-the-curve (AUC) of 0.95.

Figure 33:
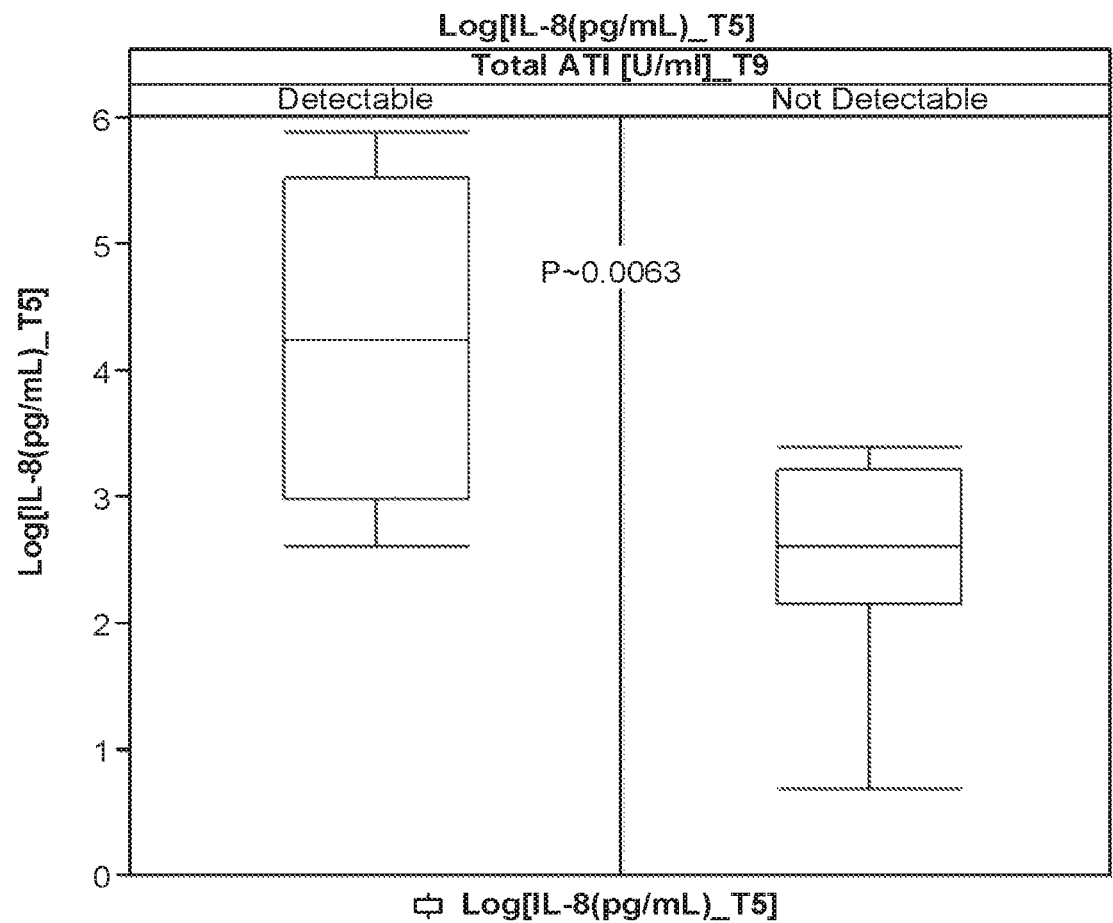
FIG. 33 shows the association between IL-8 levels at T5 (week 2) and ATI formation at T9 (i.e., by week 6 or within the first 6 weeks of IFX therapy).

FIG. 33 shows the association between IL-8 levels at T5 and ATI formation at T9. In particular, elevated levels of IL-8 at T5 (week 2) were associated with ATI formation at T9 (i.e., by week 6 or within the first 6 weeks of IFX therapy). These results illustrate that IL-8 levels at week 2 can be used to predict ATI formation by week 6.

Figure 34:
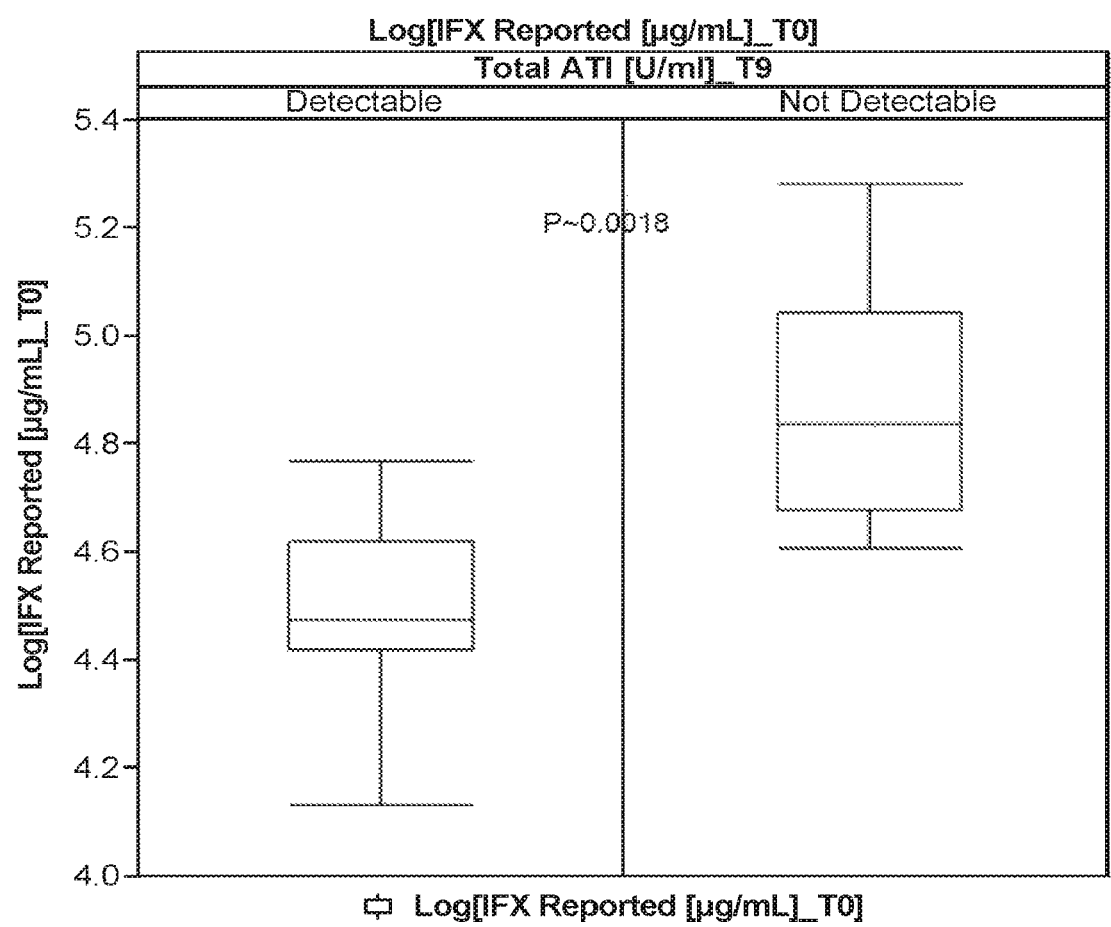
FIG. 34 shows the association between IFX levels at T0 (24 hours after dosing) and ATI formation at T9 (i.e., by week 6 or within the first 6 weeks of IFX therapy).

FIG. 34 shows the association between IFX levels at T0 and ATI formation at T9. In particular, low levels of IFX at T0 (24 hours after dosing) were associated with ATI formation at T9 (i.e., by week 6 or within the first 6 weeks of IFX therapy). These results illustrate that IFX levels 24 hours after dosing can be used to predict ATI formation by week 6.

Figure 35:
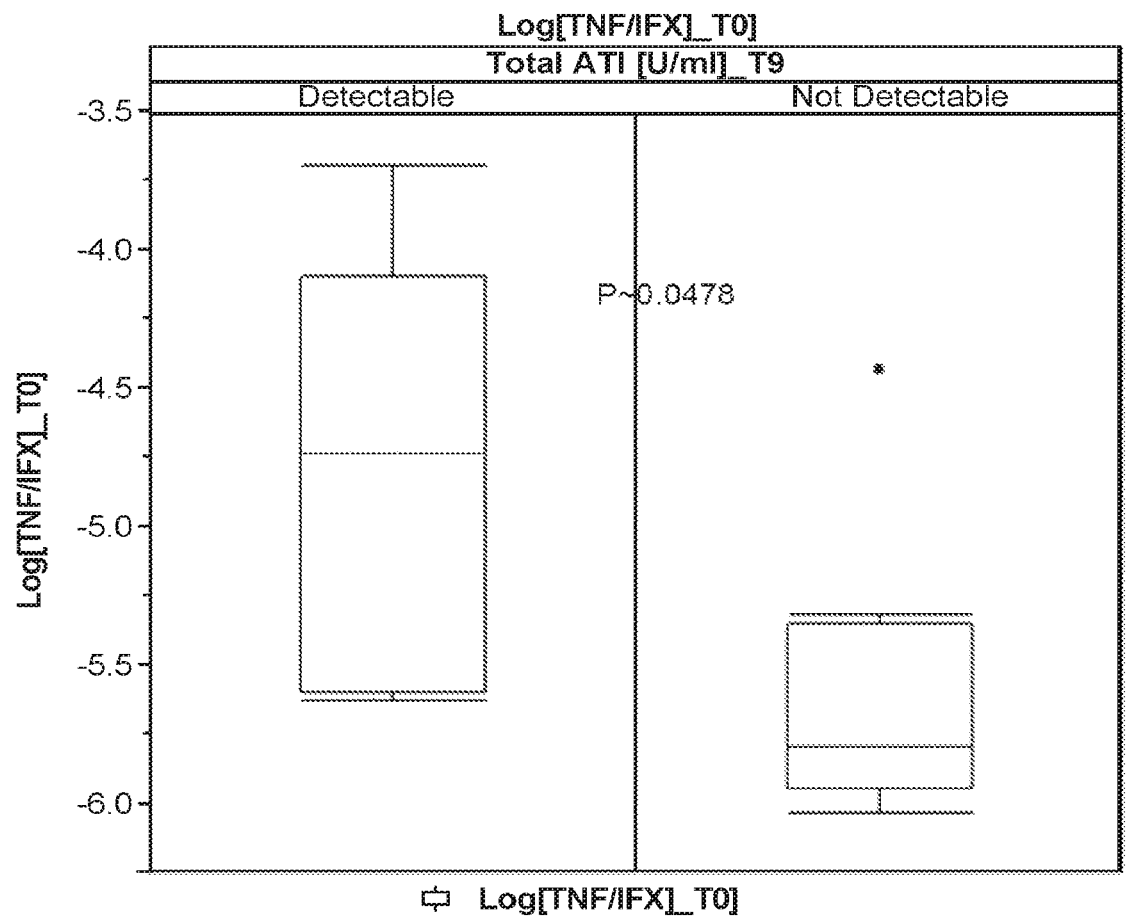
FIG. 35 shows the association between the ratio of TNFα levels to IFX levels (i.e., TNFα/IFX ratio) at T0 (24 hours after dosing) and ATI formation at T9 (i.e., by week 6 or within the first 6 weeks of IFX therapy).

FIG. 35 shows the association between the ratio of TNFα levels to IFX levels (i.e., TNFα/IFX ratio) at T0 and ATI formation at T9. In particular, higher TNFα/IFX ratios at T0 (24 hours after dosing) were associated with ATI formation at T9 (i.e., by week 6 or within the first 6 weeks of IFX therapy). These results illustrate that determining a ratio of TNFα/IFX levels 24 hours after dosing can be used to predict ATI formation by week 6.

FIG. 36 shows the results of multiple regression modelling to predict ATI formation at T9. In particular, FIG. 36 illustrates that the use of IL-8 levels at T5 (week 2) together with IFX levels at T0 (24 hours after dosing) as the predictor variables was capable of predicting ATI formation by week 6 (i.e., within the first 6 weeks of IFX therapy).

Figure 37:
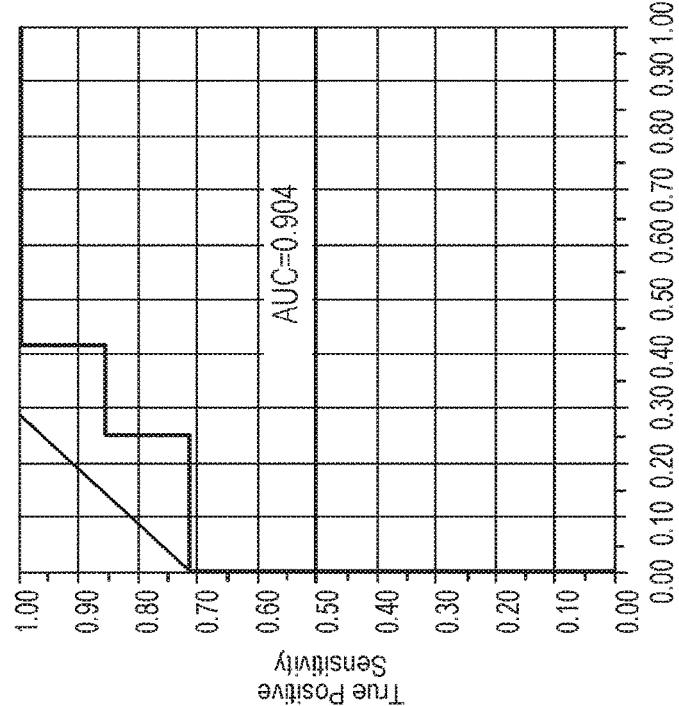
FIG. 37 shows the results of multiple regression modelling using IL-8 levels together with TNFα/IFX ratio to predict ATI formation at T9 (i.e., by week 6 or within the first 6 weeks of IFX therapy).

FIG. 37 shows the results of multiple regression modelling to predict ATI formation at T9. In particular, FIG. 37 illustrates that the use of IL-8 levels at T5 (week 2) together with the ratio of TNFα levels to IFX levels (i.e., TNFα/IFX ratio) at T0 (24 hours after dosing) as the predictor variables provided a prediction of ATI formation by week 6 (i.e., within the first 6 weeks of IFX therapy) with an area-under-the-curve (AUC) of 0.904.

Accordingly, this example demonstrates that IL-8 and IL12p40 are associated with endoscopic response at week 8, and that IL-8 and IFX levels predict ATI formation at T9. Notably, this example shows that IL-8 is an important predictor for both endoscopic response as well as ATI formation.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for predicting whether a subject having an inflammatory bowel disease will later develop autoantibodies to an anti-TNFα drug during a course of therapy with the anti-TNFα drug, the method comprising determining one or more predictor variables comprising (i) a level of IL-8 and a level of the anti-TNFα drug, (ii) a level of IL-8 and a TNFα/drug ratio, (iii) a level of IL-8, (iv) a TNFα/drug ratio, (v) a level of the anti-TNFα drug and a TNFα/drug ratio, or (vi) a level of IL-8, a level of the anti-TNFα drug, and a TNFα/drug in one or more samples obtained from the subject at least 24 hours following induction with the anti-TNFα drug;

comparing the one or more predictor variables to a reference level for each of the one or more predictor variables;

predicting the subject will develop autoantibodies to the anti-TNFα drug based on the one or more predictor variables compared to the reference level for each of the one or more predictor variables; and administering a modified dose of the anti-TNFα drug to the subject, administering a different type of the anti-TNFα drug to the subject, or administering an immunosuppressive agent to the subject.

2. The method of claim 1, wherein the subject has ulcerative colitis (UC).

3. The method of claim 1, wherein at least one of the one or more samples is obtained from the subject 24 hours following induction with the anti-TNFα drug.

4. The method of claim 1, wherein the autoantibodies are predicted to develop within 6 weeks following induction with the anti-TNFα drug.

5. The method of claim 1, wherein the method further comprises applying a statistical analysis on the one or more predictor variables.

6. The method of claim 5, wherein the statistical analysis predicts whether the subject will later develop autoantibodies to the anti-TNFα drug.

7. The method of claim 1, wherein at least one of the one or more samples is obtained from the subject 2 weeks following induction with the anti-TNFα drug.

8. The method of claim 1, wherein at least one of the one or more samples is obtained from the subject at least 2 weeks following induction with the anti-TNFα drug.

9. The method of claim 1, wherein the sample is whole blood, serum, or plasma.

10. The method of claim 1, wherein the immunosuppressive agent comprises methotrexate or azathioprine.

11. The method of claim 1, wherein the anti-TNFα drug comprises etanercept, adalimumab, certolizumab pegol, golimumab, or infliximab.

12. The method of claim 1, wherein the anti-TNFα drug comprises infliximab.

13. The method of claim 1, wherein the autoantibodies comprise human anti-chimeric antibodies, human anti-humanized antibodies, or human anti-mouse antibodies.

14. The method of claim 1, further comprising determining two or three of the one or more predictor variables, wherein the two or three of the one or more predictor variables are obtained in two or three separate samples obtained from the subject.

15. The method of claim 14, wherein the separate samples are obtained from the subject at separate time points following induction with the anti-TNFα drug.

16. The method of claim 1, further comprising predicting that the subject will later develop autoantibodies to the anti-TNFα drug.

* * * * *